US008689614B2

(12) United States Patent
Day et al.

(10) Patent No.: US 8,689,614 B2
(45) Date of Patent: Apr. 8, 2014

(54) APPARATUS AND METHOD FOR DETERMINING THE RESULTS OF ASSAYS

(75) Inventors: Richard Day, Inverness (GB); Emma Day, Inverness (GB)

(73) Assignee: Highland Biosciences Limited, Inverness (GB)

( * ) Notice: Subject to any disclaimer, the term of this patent is extended or adjusted under 35 U.S.C. 154(b) by 1030 days.

(21) Appl. No.: 12/675,051

(22) PCT Filed: Aug. 26, 2008

(86) PCT No.: PCT/GB2008/050738
§ 371 (c)(1),
(2), (4) Date: Mar. 31, 2010

(87) PCT Pub. No.: WO2009/027735
PCT Pub. Date: Mar. 5, 2009

(65) Prior Publication Data
US 2011/0129929 A1    Jun. 2, 2011

(30) Foreign Application Priority Data
Aug. 24, 2007 (GB) .................................. 0716542.6

(51) Int. Cl.
*G01N 11/00* (2006.01)
(52) U.S. Cl.
USPC ......... 73/54.01; 73/54.41; 435/13; 435/283.1
(58) Field of Classification Search
USPC ............... 73/54.04, 54.11, 54.24–27; 435/13, 435/283.1; 436/8–19
See application file for complete search history.

(56) References Cited

U.S. PATENT DOCUMENTS

| 4,469,979 A | 9/1984 | Chuang |
| 4,594,898 A | 6/1986 | Kirman et al. |
| 4,878,386 A | 11/1989 | Isobe et al. |
| 4,920,787 A | 5/1990 | Dual et al. |
| 4,922,745 A | 5/1990 | Rudkin et al. |
| 4,947,694 A | 8/1990 | Kirman et al. |
| 5,020,370 A | 6/1991 | Deval et al. |

(Continued)

FOREIGN PATENT DOCUMENTS

| EP | 0112156 | 6/1984 |
| EP | 0282251 | 9/1988 |

(Continued)

OTHER PUBLICATIONS

Green, "Thesis"; Brunel University, 1995.

(Continued)

*Primary Examiner* — Hezron E Williams
*Assistant Examiner* — Hoang Nguyen
(74) *Attorney, Agent, or Firm* — Moore & Van Allen PLLC; W. Kevin Ransom

(57) ABSTRACT

The present invention provides a method for the real-time continuous monitoring of a change or density and/or viscosity within a test sample. Such methods can be used to determine the occurrence of a chemical reaction within a test sample where the same causes and increase or decrease in the density and/or viscosity of the sample due to, for example, a gelation, precipitation or coagulation occurring within the test sample. There is further provided a multi-resonator apparatus for use in measuring the density and/or viscosity of a test sample in which the multi-beam resonator is immersed.

46 Claims, 33 Drawing Sheets

(56) References Cited

U.S. PATENT DOCUMENTS

| | | | |
|---|---|---|---|
| 5,095,763 A | 3/1992 | Delatorre | |
| 5,211,054 A | 5/1993 | Muramatsu et al. | |
| 5,892,144 A | 4/1999 | Meller et al. | |
| 5,962,786 A | 10/1999 | Le Traon et al. | |
| 5,987,987 A | 11/1999 | Watarai | |
| 6,044,694 A | 4/2000 | Anderson et al. | |
| 6,046,051 A | 4/2000 | Jina | |
| 6,200,532 B1* | 3/2001 | Wu et al. | 422/73 |
| 6,311,549 B1 | 11/2001 | Thundat et al. | |
| 6,336,353 B2 | 1/2002 | Matsiev et al. | |
| 6,360,600 B1 | 3/2002 | Kuroki | |
| 6,401,519 B1 | 6/2002 | McFarland et al. | |
| 6,412,354 B1 | 7/2002 | Birchak et al. | |
| 6,746,872 B2 | 6/2004 | Zheng et al. | |
| 6,904,786 B2 | 6/2005 | Matsiev et al. | |
| 6,907,785 B1* | 6/2005 | Gallagher | 73/579 |
| 7,043,969 B2 | 5/2006 | Matsiev et al. | |
| 7,073,370 B2 | 7/2006 | Matsiev et al. | |
| 7,178,378 B2 | 2/2007 | Crawley et al. | |
| 7,334,452 B2 | 2/2008 | Matsiev et al. | |
| 7,562,557 B2 | 7/2009 | Bennett et al. | |
| 7,674,616 B2* | 3/2010 | Farnam et al. | 435/287.1 |
| 2002/0174730 A1 | 11/2002 | Drahm et al. | |
| 2004/0099050 A1 | 5/2004 | Matsiev et al. | |
| 2004/0244487 A1 | 12/2004 | Kolosov et al. | |
| 2005/0209796 A1 | 9/2005 | Kolosov et al. | |
| 2005/0244299 A1 | 11/2005 | Dasgupta et al. | |
| 2006/0010964 A1 | 1/2006 | Sparks et al. | |
| 2006/0035298 A1 | 2/2006 | Hill et al. | |
| 2006/0110283 A1* | 5/2006 | Fish | 422/52 |
| 2006/0170311 A1* | 8/2006 | Jones et al. | 310/338 |
| 2006/0213552 A1 | 9/2006 | Sparks et al. | |
| 2006/0218996 A1 | 10/2006 | Matsiev et al. | |
| 2006/0243591 A1* | 11/2006 | Plotkin et al. | 204/403.04 |
| 2006/0246214 A1* | 11/2006 | Plotkin et al. | 427/58 |
| 2006/0281140 A1 | 12/2006 | Ranby | |
| 2007/0017291 A1 | 1/2007 | Cypes et al. | |
| 2007/0077610 A1 | 4/2007 | Ghai et al. | |
| 2007/0144240 A1 | 6/2007 | Andle | |
| 2008/0110247 A1 | 5/2008 | Shaw et al. | |
| 2010/0015649 A1* | 1/2010 | Day | 435/13 |
| 2010/0206727 A1* | 8/2010 | Cardosi et al. | 204/400 |
| 2011/0005941 A1* | 1/2011 | Blythe et al. | 205/777.5 |

FOREIGN PATENT DOCUMENTS

| | | |
|---|---|---|
| EP | 0304283 | 2/1989 |
| EP | 0737853 | 10/1996 |
| EP | 0943091 | 4/1999 |
| EP | 1329723 A2 | 7/2003 |
| EP | 1443325 A1 | 8/2004 |
| EP | 1588161 A | 8/2004 |
| EP | 1519162 | 3/2005 |
| EP | 1740318 A | 11/2005 |
| EP | 1674865 | 6/2006 |
| EP | 1674865 A1 | 6/2006 |
| EP | 1804048 | 7/2007 |
| EP | 1901065 A1 | 3/2008 |
| GB | 2075762 | 11/1981 |
| GB | 2280751 A | 2/1995 |
| GB | 2303450 A | 2/1997 |
| GB | 2445163 | 7/2008 |
| JP | 11094726 | 4/1999 |
| SU | 682796 | 8/1979 |
| SU | 744277 | 6/1980 |
| SU | 759908 | 8/1980 |
| SU | 898288 | 1/1982 |
| WO | WO94/14047 | 6/1994 |
| WO | WO98/09139 | 3/1998 |
| WO | WO99/18431 | 4/1999 |
| WO | WO00/04370 | 1/2000 |
| WO | WO00/31529 | 6/2000 |
| WO | WO-2004/036191 A1 | 4/2004 |
| WO | WO2004/036207 | 4/2004 |
| WO | WO2004/070335 | 8/2004 |
| WO | WO2004/086002 | 10/2004 |
| WO | WO-2004/086003 A1 | 10/2004 |
| WO | WO-2004/086027 A2 | 10/2004 |
| WO | WO2004/094987 | 11/2004 |
| WO | WO-2005/043126 A2 | 5/2005 |
| WO | WO-2005/103645 A2 | 11/2005 |
| WO | WO2005/103674 | 11/2005 |
| WO | WO2005/114138 | 12/2005 |
| WO | WO2006/031072 | 3/2006 |
| WO | WO2006/067504 | 6/2006 |
| WO | WO2006/094694 | 9/2006 |
| WO | WO2007/034152 | 3/2007 |
| WO | WO2007/077038 | 7/2007 |
| WO | WO-2007/101993 A2 | 9/2007 |
| WO | WO2008/081181 A1 | 7/2008 |

OTHER PUBLICATIONS

E. Benes et al., "Sensors based on piezoelectric resonators"; Sensors and Actuators A, vol. 48, No. 1, May 1, 1995, pp. 1-21.

Reichel et al, "Measurement of Liquid Properties Using a Vibrating Micromachined Clamped-Clamped Beam Structure"; Sensor Conference 2007 Proceedings II, pp. 33-38.

Eernise et al.; "Survey of Quartz Bulk Resonator Sensor Technologies"; IEEE TRANS on Ultrasonics, Ferroelectrics and Frequency Control, vol. 35, No. 3, May 1988, p. 323.

Torah et al.; "A Study of powder size combinations for improving piezo electric properties of PZT thick-film devices the 17th European Conference on Solid State Transducers (Eurosensors XVII)"; Sep. 21-24, 2003, Portugal. pp. 610-613.

Zhang et al.; "Determination of liquid density with a low frequency mechanical sensor based on quartz tuning fork"; Sensors and Actuators B 84 (2002) 123-128.

Cheshmehdoost et al.; "Characteristics of a force transducer incorporating a mechanical DETF resonator"; Sensors and Actuators A vol. 26, No. 1-3, Mar. 1, 1991, pp. 307-312.

Langdon et al.; "Resonator sensors—a review;" Journal of Physics E Scientific Instruments. vol. 18, No. 2, Feb. 1, 1985, pp. 103-115.

Dring et al.; "Integrated on-line multisensing of fluid flow using a mechanical resonator"; Sensors and Actuators vol. 85, No. 1-3, Aug. 25, 2000, pp. 275-279.

Ward et al.; IEEE Transactions on Ultrasonics, Ferroelectrics and Frequency Control, vol. 35, No. 3, May 1988; pp. 323-330.

Green et al., "Liquid Density Measurements using a Double-Ended Tuning Fork Resonator"; Proceedings of International IMEKO Conference ISMQC 95/CIMI 95, Zaragoza, Oct. 1995, pp. 401-410.

Green et al., "Measurement of Liquid Density Using a Double-Ended Tuning Fork Resonator, Measurement and Control"; vol. 29, Sep. 1996, pp. 208-210.

Nicu et al.; "Modeling of a tuning fork biosensor based on the excitation of one particular resonance mode"; IOP Publishing J. Micromech. Microeng. 14 (2004) 727-736.

Cotton et al.; "A new binderless thick-film piezoelectric paste"; J Mater Sci.: Mater Electron (2007) 18:1037-1044.

International Search Report for PCT/GB2008/050738, dated Jul. 1, 2009.

Lavrik et al., "Cantilever transducers as a platform for chemical and biological sensors", Review of Scientific Instruments, vol. 75, No. 7, Jul. 2004.

Beeby, "Mechanical Transduction Techniques", MEMS Mechanical Sensors, Chapter 5, Artech Books 2004, pp. 85-112.

Su et al., "Quartz tuning fork biosensor", Biosensors and Bioelectronics, vol. 17, 2002, pp. 111-117.

Reisch et al., "A Novel Sensor System for Liquid Properties Based on a Micromachined Beam and a Low-Cost Optical Readout", IEEE Sensors 2007 Conference, pp. 872-875.

Etchart et al., "MEMS sensors for density-viscosity sensing in a low-flow microfluidic environment", Sensors and Actuators vol. A 141, 2008, pp. 266-275.

Dring et al., "Integrated on-line multisensing of fluid flow using a mechanical resonator", Sensors and Actuators, vol. 85, 2000, pp. 275-279.

(56) References Cited

OTHER PUBLICATIONS

Shih et al., "Simultaneous liquid viscosity and density determination with piezoelectric unimorph cantilevers", Journal of Applied Physics, vol. 89 No. 2, Jan. 15, 2001, pp. 1497-1505.

Tamayo et al., "Chemical sensors and biosensors in liquid environment based on microcantilevers with amplified quality factor", Ultramicroscopy, vol. 86, 2001, pp. 167-173.

Tamayo et al., "Digital tuning of the quality factor of micromechanical resonant biological detectors", Sensors and Actuators, vol. B 89, 2003, pp. 33-39.

Yan et al., "Metallic Triple Beam Resonator with Thick-film Printed Drive and Pickup", At *The 17th European Conference on Solid State Transducers (Eurosensors XVII)*, Guimaraes, Portugal, Sep. 21-24, 2003. University of Minho, pp. 10-13.

Seo et al., "Novel High Q-Factor Resonant Microsensor Platform for Chemical and Biological Applications", Transducers '05 at the $13^{th}$ International Conference on Solid-State Sensors Actuators and MicroSystems, Seoul, Korea, Jun. 5-9, 2005, pp. 593-596.

Gfeller et al., "Rapid Biosensor for Detection of Antibiotic-Selective Growth of *Escherichia coli*", Applied and Environmental Microbiology, vol. 71, No. 5, May 2005, pp. 2626-2631.

Burg et al., "Vacuum-Packaged Suspended Microchannel Resonant Mass Sensor for Biomolecular Detection", Journal of Microelectromechanical Systems, vol. 15, No. 6, Dec. 2006, pp. 1466-1476.

\* cited by examiner

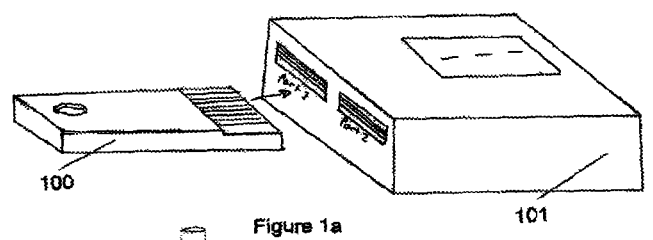
Figure 1a
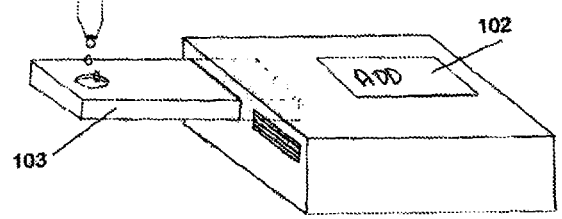
Figure 1b
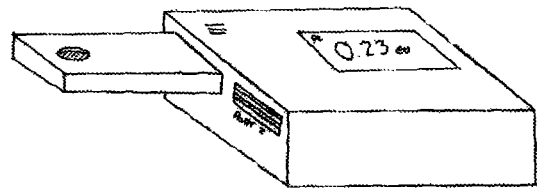
Figure 1c
Figure 1

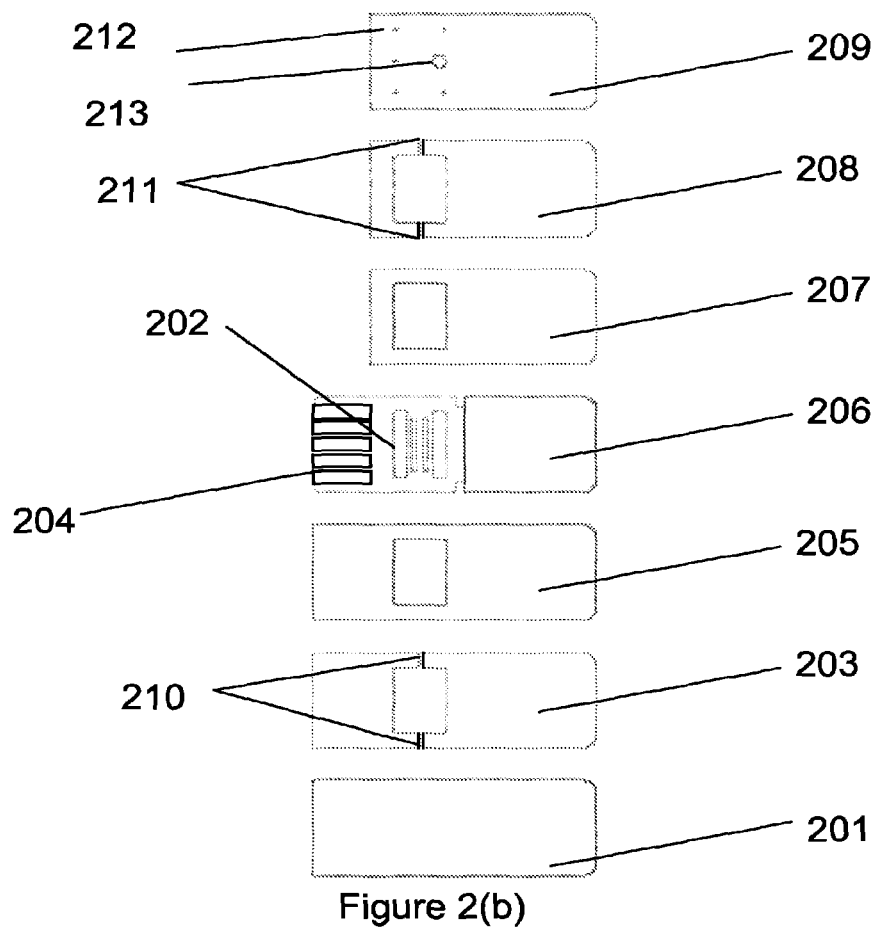
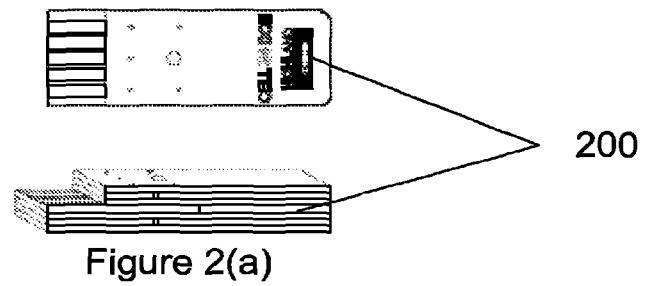
Figure 2(b)
Figure 2(a)

Key

-a     centre beam width
-b     beam length
-c     distance between beams
-d     beam mounting zone
-e     gap between outer beam and device housing

| Design name: | Cell 1 DOE | Cell 2 DOE | Cell 3 DOE | Cell 4 DOE | Cell 5 DOE | Cell 6 DOE | Cell 7 DOE | Cell 8 DOE |
|---|---|---|---|---|---|---|---|---|
| Centre beam width | 1 | 1 | 1 | 1 | 1 | 1 | 1 | 1 |
| Gap to frame | 0.5 | 0.5 | 0.5 | 0.5 | 0.5 | 0.5 | 0.5 | 0.5 |
| Beam length | 5.5 | 7 | 5.5 | 5.5 | 7 | 8.5 | 8.5 | 8.5 |
| Gap between beams | 0.25 | 0.5 | 0.75 | 0.25 | 0.5 | 0.25 | 0.75 | 0.75 |
| Overall length | 8.5 | 8.5 | 8.5 | 12.4 | 10.45 | 12.4 | 12.4 | 10.45 |
| Beam mounting zone | 1.5 | 0.75 | 1.5 | 3.45 | 1.725 | 1.95 | 1.95 | 0.975 |
| Ratio of beam length: mounting zone | 3.67 | 9.33 | 3.67 | 1.59 | 4.06 | 4.36 | 4.36 | 8.72 |
| Overall cell length | 8.50 | 8.50 | 8.50 | 12.40 | 10.45 | 12.40 | 12.40 | 10.45 |
| Overall cell width | 3.50 | 4.00 | 4.50 | 3.50 | 4.00 | 3.50 | 4.50 | 4.50 |

Figure 7(a)

| Design name: | Cell 9 DOE | Cell 10 DOE | Cell 11 DOE | Cell 12 DOE | Cell 13 DOE | Cell 14 DOE | Cell 15 DOE | Cell 16 DOE |
|---|---|---|---|---|---|---|---|---|
| Centre beam width | 1 | 1 | 1 | 1 | 1 | 1 | 1 | 1 |
| Gap to frame | 1 | 1 | 1 | 1 | 1 | 1 | 1 | 1 |
| Beam length | 5.5 | 7 | 5.5 | 5.5 | 7 | 8.5 | 8.5 | 8.5 |
| Gap between beams | 0.25 | 0.5 | 0.75 | 0.25 | 0.5 | 0.25 | 0.75 | 0.75 |
| Overall length | 8.5 | 8.5 | 8.5 | 12.4 | 10.45 | 12.4 | 12.4 | 10.45 |
| Beam mounting zone | 1.5 | 0.75 | 1.5 | 3.45 | 1.725 | 1.95 | 1.95 | 0.975 |
| Ratio of beam length: mounting zone | 3.67 | 9.33 | 3.67 | 1.59 | 4.06 | 4.36 | 4.36 | 8.72 |
| Overall cell length | 8.50 | 8.50 | 8.50 | 12.40 | 10.45 | 12.40 | 12.40 | 10.45 |
| Overall cell width | 4.50 | 5.00 | 5.50 | 4.50 | 5.00 | 4.50 | 5.50 | 5.50 |

Figure 7(b)

| Design name: | Cell 17 DOE | Cell 18 DOE | Cell 19 DOE | Cell 20 DOE | Cell 21 DOE | Cell 22 DOE | Cell 23 DOE | Cell 24 DOE |
|---|---|---|---|---|---|---|---|---|
| Centre beam width | 1 | 1 | 1 | 1 | 1 | 1 | 1 | 1 |
| Gap to frame | 2 | 2 | 2 | 2 | 2 | 2 | 2 | 2 |
| Beam length | 5.5 | 7 | 5.5 | 5.5 | 7 | 8.5 | 8.5 | 8.5 |
| Gap between beams | 0.25 | 0.5 | 0.75 | 0.25 | 0.5 | 0.25 | 0.75 | 0.75 |
| Overall length | 8.5 | 8.5 | 8.5 | 12.4 | 10.45 | 12.4 | 12.4 | 10.45 |
| Beam mounting zone | 1.5 | 0.75 | 1.5 | 3.45 | 1.725 | 1.95 | 1.95 | 0.975 |
| Ratio of beam length: mounting zone | 3.67 | 9.33 | 3.67 | 1.59 | 4.06 | 4.36 | 4.36 | 8.72 |
| Overall cell length | 8.50 | 8.50 | 8.50 | 12.40 | 10.45 | 12.40 | 12.40 | 10.45 |
| Overall cell width | 6.50 | 7.00 | 7.50 | 6.50 | 7.00 | 6.50 | 7.50 | 7.50 |

Figure 7(c)

| Design name: | Cell 25 DOE | Cell 26 DOE | Cell 27 DOE | Cell 28 DOE | Cell 29 DOE | Cell 30 DOE | Cell 31 DOE | Cell 32 DOE |
|---|---|---|---|---|---|---|---|---|
| Centre beam width | 2 | 2 | 2 | 2 | 2 | 2 | 2 | 2 |
| Gap to frame | 0.5 | 0.5 | 0.5 | 0.5 | 0.5 | 0.5 | 0.5 | 0.5 |
| Beam length | 5.5 | 7 | 5.5 | 5.5 | 7 | 8.5 | 8.5 | 8.5 |
| Gap between beams | 0.25 | 0.5 | 0.75 | 0.25 | 0.5 | 0.25 | 0.75 | 0.75 |
| Overall length | 8.5 | 8.5 | 8.5 | 12.4 | 10.45 | 12.4 | 12.4 | 10.45 |
| Beam mounting zone | 1.5 | 0.75 | 1.5 | 3.45 | 1.725 | 1.95 | 1.95 | 0.975 |
| Ratio of beam length: mounting zone | 3.67 | 9.33 | 3.67 | 1.59 | 4.06 | 4.36 | 4.36 | 8.72 |
| Overall cell length | 8.50 | 8.50 | 8.50 | 12.40 | 10.45 | 12.40 | 12.40 | 10.45 |
| Overall cell width | 5.50 | 6.00 | 6.50 | 5.50 | 6.00 | 5.50 | 6.50 | 6.50 |

Figure 7(d)

| Design name: | Cell 33 DOE | Cell 34 DOE | Cell 35 DOE | Cell 36 DOE | Cell 37 DOE | Cell 38 DOE | Cell 39 DOE | Cell 40 DOE |
|---|---|---|---|---|---|---|---|---|
| Centre beam width | 2 | 2 | 2 | 2 | 2 | 2 | 2 | 2 |
| Gap to frame | 1 | 1 | 1 | 1 | 1 | 1 | 1 | 1 |
| Beam length | 5.5 | 7 | 5.5 | 5.5 | 7 | 8.5 | 8.5 | 8.5 |
| Gap between beams | 0.25 | 0.5 | 0.75 | 0.25 | 0.5 | 0.25 | 0.75 | 0.75 |
| Overall length | 8.5 | 8.5 | 8.5 | 12.4 | 10.45 | 12.4 | 12.4 | 10.45 |
| Beam mounting zone | 1.5 | 0.75 | 1.5 | 3.45 | 1.725 | 1.95 | 1.95 | 0.975 |
| Ratio of beam length: mounting zone | 3.67 | 9.33 | 3.67 | 1.59 | 4.06 | 4.36 | 4.36 | 8.72 |
| Overall cell length | 8.50 | 8.50 | 8.50 | 12.40 | 10.45 | 12.40 | 12.40 | 10.45 |
| Overall cell width | 6.50 | 7.00 | 7.50 | 6.50 | 7.00 | 6.50 | 7.50 | 7.50 |

Figure 7(e)

| Design name: | Cell 41 DOE | Cell 42 DOE | Cell 43 DOE | Cell 44 DOE | Cell 45 DOE | Cell 46 DOE | Cell 47 DOE | Cell 48 DOE |
|---|---|---|---|---|---|---|---|---|
| Centre beam width | 2 | 2 | 2 | 2 | 2 | 2 | 2 | 2 |
| Gap to frame | 2 | 2 | 2 | 2 | 2 | 2 | 2 | 2 |
| Beam length | 5.5 | 7 | 5.5 | 5.5 | 7 | 8.5 | 8.5 | 8.5 |
| Gap between beams | 0.25 | 0.5 | 0.75 | 0.25 | 0.5 | 0.25 | 0.75 | 0.75 |
| Overall length | 8.5 | 8.5 | 8.5 | 12.4 | 10.45 | 12.4 | 12.4 | 10.45 |
| Beam mounting zone | 1.5 | 0.75 | 1.5 | 3.45 | 1.725 | 1.95 | 1.95 | 0.975 |
| Ratio of beam length: mounting zone | 3.67 | 9.33 | 3.67 | 1.59 | 4.06 | 4.36 | 4.36 | 8.72 |
| Overall cell length | 8.50 | 8.50 | 8.50 | 12.40 | 10.45 | 12.40 | 12.40 | 10.45 |
| Overall cell width | 8.50 | 9.00 | 9.50 | 8.50 | 9.00 | 8.50 | 9.50 | 9.50 |

Figure 7(f)

| Family | Sensor | Beam length | Overall length | Design ratio: beam : mounting zone | Gap between beams | Beam width | Gap to frame | Mode | Q factor sensitivity | Frequency sensitivity |
|---|---|---|---|---|---|---|---|---|---|---|
| 1 | Design 4 | 5.5 | 12.4 | 1.59 | 0.25 | 1 | 0.5 | 1 | 8 | 521 |
|  | Design 12 | 5.5 | 12.4 | 1.59 | 0.25 | 1 | 1 | 1 | 16 | 1678 |
|  | Design 20 | 5.5 | 12.4 | 1.59 | 0.25 | 1 | 2 | 1 | 2 | #N/A |
|  | Design 28 | 5.5 | 12.4 | 1.59 | 0.25 | 2 | 0.5 | 1 | 25 | 1948 |
| 2 | Design 1 | 5.5 | 8.5 | 3.67 | 0.25 | 1 | 0.5 | 3 | 146 | 952 |
|  | Design 3 | 5.5 | 8.5 | 3.67 | 0.75 | 1 | 0.5 | 3 | 87 | 872 |
|  | Design 9 | 5.5 | 8.5 | 3.67 | 0.25 | 1 | 1 | 3 | 96 | 865 |
|  | Design 11 | 5.5 | 8.5 | 3.67 | 0.75 | 1 | 1 | 3 | 15 | 590 |
|  | Design 17 | 5.5 | 8.5 | 3.67 | 0.25 | 1 | 2 | 3 | 52 | 760 |
|  | Design 19 | 5.5 | 8.5 | 3.67 | 0.75 | 1 | 2 | 1 | 21 | 568 |
|  | Design 33 | 5.5 | 8.5 | 3.67 | 0.25 | 2 | 1 | 3 | 84 | 74 |
|  | Design 35 | 5.5 | 8.5 | 3.67 | 0.75 | 2 | 1 | 3 | 31 | 14 |
| 3 | Design 13 | 7 | 10.45 | 4.06 | 0.5 | 1 | 1 | 3 | 106 | 712 |
|  | Design 5 | 7 | 10.45 | 4.06 | 0.5 | 1 | 0.5 | 1 | 31 | 1183 |
|  | Design 21 | 7 | 10.45 | 4.06 | 0.5 | 1 | 2 | 1 | 75 | 664 |
|  | Design 37 | 7 | 10.45 | 4.06 | 0.5 | 2 | 1 | 3 | 62 | 376 |
| 4 | Design 6 | 8.5 | 12.4 | 4.36 | 0.25 | 1 | 0.5 | 1 | #N/A | 356 |
|  | Design 7 | 8.5 | 12.4 | 4.36 | 0.75 | 1 | 0.5 | 1 | 38 | 413 |
|  | Design 14 | 8.5 | 12.4 | 4.36 | 0.25 | 1 | 1 | 3 | 97 | 420 |
|  | Design 15 | 8.5 | 12.4 | 4.36 | 0.75 | 1 | 1 | 1 | #N/A | 454 |
|  | Design 22 | 8.5 | 12.4 | 4.36 | 0.25 | 1 | 2 | 3 | 43 | 407 |
|  | Design 23 | 8.5 | 12.4 | 4.36 | 0.75 | 1 | 2 | 3 | 77 | 398 |
| 5 | Design 8 | 8.5 | 10.45 | 8.72 | 0.75 | 1 | 0.5 | 3 | 66 | 926 |
|  | Design 16 | 8.5 | 10.45 | 8.72 | 0.75 | 1 | 1 | 1 | 34 | 635 |
|  | Design 24 | 8.5 | 10.45 | 8.72 | 0.75 | 1 | 2 | 3 | 82 | 520 |
|  | Design 40 | 8.5 | 10.45 | 8.72 | 0.75 | 2 | 1 | 1 | 60 | 325 |
| 6 | Design 2 | 7 | 8.5 | 9.33 | 0.5 | 1 | 0.5 | 3 | 97 | 447 |
|  | Design 10 | 7 | 8.5 | 9.33 | 0.5 | 1 | 1 | 1 | 43 | 1122 |
|  | Design 18 | 7 | 8.5 | 9.33 | 0.5 | 1 | 2 | 3 | 83 | 1310 |
|  | Design 26 | 7 | 8.5 | 9.33 | 0.5 | 2 | 0.5 | 3 | 53 | 56 |
|  | Design 34 | 7 | 8.5 | 9.33 | 0.5 | 2 | 1 | 3 | 68 | 514 |

Figure 15

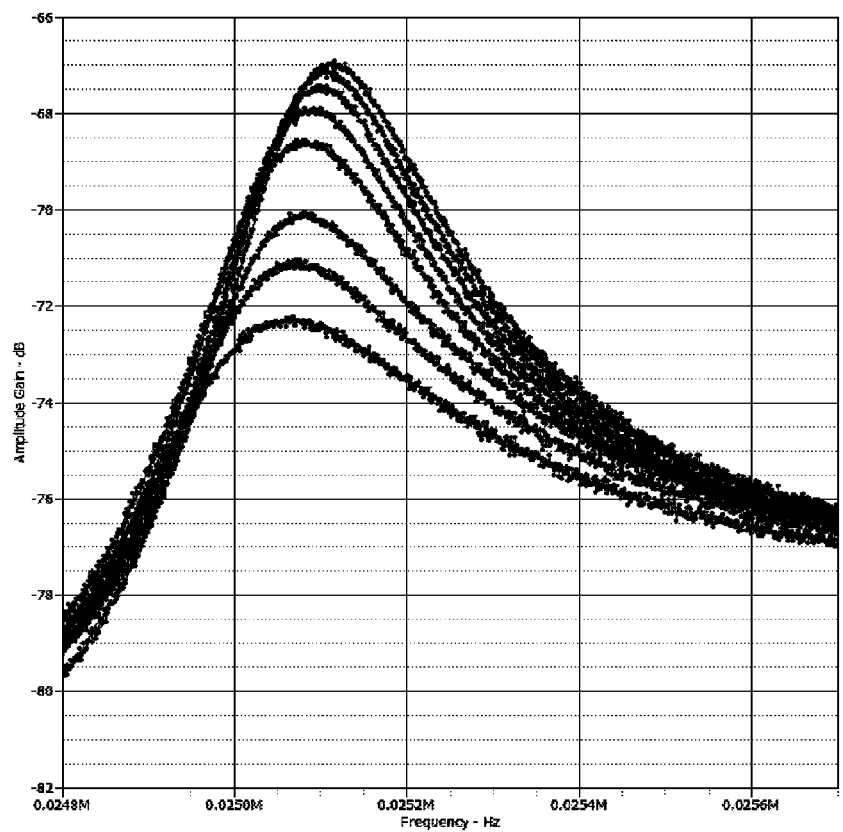
Figure 23(a) 0.1EU

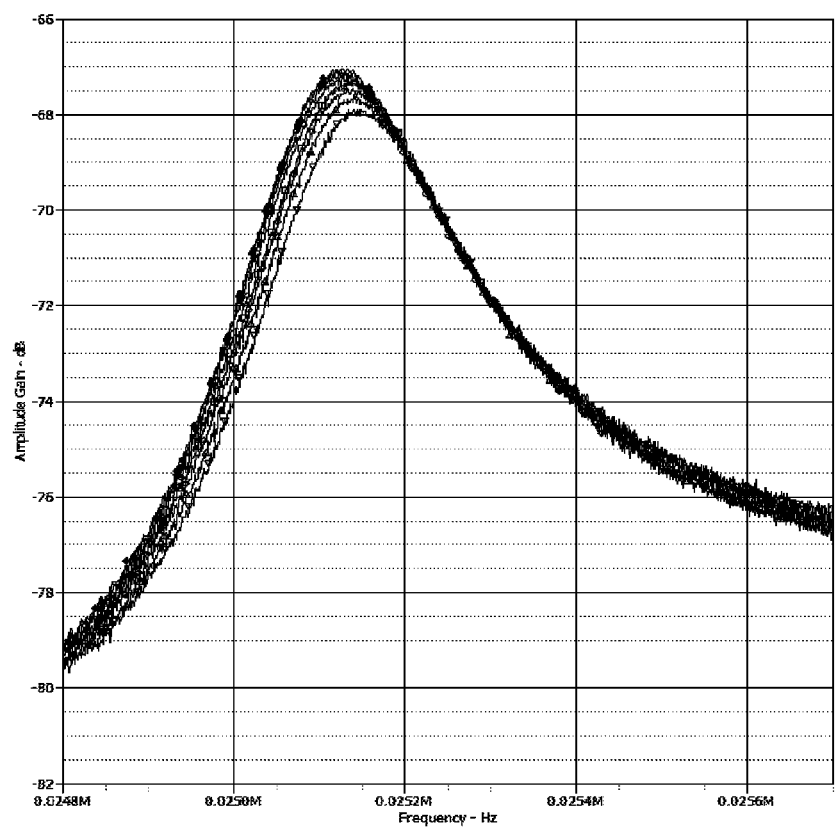
Figure 23(b) 0EU

APPARATUS AND METHOD FOR DETERMINING THE RESULTS OF ASSAYS

FIELD OF THE INVENTION

The present invention provides an improved sensor apparatus for the measurement of assays and chemical reactions wherein a change in viscosity and/or density, by for example, gellation, precipitation, agglutination or coagulation, occurs. In particular, there is provided a biosensor for use in the real time measurement of an assay, such as an endotoxin assay used to determine the presence of microbial contaminants in a test sample, the apparatus allowing the viscosity and/or density of the sample to be measured continuously as the assay progresses. The invention further extends to methods for performing such assays, and further to the use of said apparatus in the performance of such methods.

BACKGROUND TO THE INVENTION

The viscosity of a fluid may be measured using a viscometer. Viscometers measure the properties of a fluid under conditions where the fluid remains stationary and an object, such as a vibratory element moves through it. The measurement of the viscosity can be determined based on the drag caused by the relative motion of the fluid and surface.

One specific type of viscometer is a vibration viscometer. Vibration viscometers typically function by allowing the measurement of the dampening of an oscillating electrochemical resonator which is immersed in the fluid of which the viscosity is to be determined. The greater the viscosity of the fluid, the larger the dampening effect imposed on the resonator.

A change in the density or viscosity of a fluid can accompany or be the result of the occurrence of a chemical reaction. A change in the density or viscosity of a test sample can, in particular, occur during the performance of assays commonly used in areas such as haematology where blood clotting, or coagulation reactions are measured, in immunology where immunoassays are performed, and further for more general screening, such as high throughput screening, for example to detect the presence of a contaminant or analyte in a sample.

One example of such an assay which uses a change in density or viscosity of a test sample in order to provide result is assay based test to determine the presence of bacterial endotoxin in a test sample.

Bacterial endotoxin, such as lipopolysaccaharide (LPS), is a fever producing product of gram negative bacteria. Endotoxins typically have a hydrophobic core which is bound to repeating oligosaccharide side chains. When present in the bloodstream, even in low levels, endotoxins can cause fever, shock, hypotension, raised erythrocyte count, and disseminated intravascular coagulation. If the endotoxin is present in a sufficient high level in the bloodstream, it can cause death.

The US Food and Drug Administration department (FDA) requires drugs and pharmaceutical compounds which are to be administered to a subject either by injection, or intravenously, to undergo an endotoxin test prior to their administration. Furthermore, prosthetic devices, such as heart valves or hip replacements also require such an endotoxin test. There is therefore an on-going need to provide accurate testing to determine the presence of endotoxin within a test sample.

The traditional test used to identify the presence of pyrogens, such as endotoxin, was the rabbit pyrogen test. This test, which dates back to 1942, suffered the disadvantages of being both slow and expensive to perform. Subsequent to this, Levin and Bang discovered that blood cells (amebocytes) which were derived from the horseshoe crab (*Limulus polyphemus*), contained a clotting agent that attaches to the endotoxins produced by gram-negative bacteria. This clotting agent was identified as *Limulus* amoebocyte lysates, which is commonly abbreviated to "LAL".

LAL was used to develop a number of gellation based clotting tests which detect and quantify the presence of endotoxin within a test sample. A number of such LAL-based tests are currently used commercially to determine the presence and quantity of endotoxin within a sample.

For example, the gel-clot test is a sample test that uses a lysate preparation of *Limulus polyphemus* blood to give a positive/negative answer by means of the presence or absence of gel-clot formation within a test tube or vial. The presence of endotoxin results in clotting, and hence, this change of state can be visually determined by inverting the vessel in which the reaction has occurred.

Preparations of LAL lysate are commercially available in different sensitivities, to give a qualitative. In addition, testing kits that contain LAL reagents may be provided in 'ready to use' tube vials, which allow for diluted samples to be added to the vials so that the assay can be performed within them.

Gel-clot kits are frequently used for field testing. They may also be used in laboratories where small sample throughput is required. The maximum sensitivity of the gel-clot test is generally a level of around 0.03 EU/ml of endotoxin in a sample. However, there are disadvantages associated with such tests, in particular the cost as a large quantity of LAL reagent must be used for each sample. Furthermore, the results from the gel-clot LAL test are subject to human interpretation, as the results are visually determined. An assay based on the subjective determination of a gel-clot is particularly difficult to automate, hence determining the result of the gel-clot test in this way may introduce a greater degree of error into determining the results of the test, and may further lead to the increased risk of reporting a false negative result.

A further technique used to identify endotoxin in a sample is by means of optical analysis: chromogenic or turbidometric methods. These methods can be fully automated, and further have the advantage of providing quantitative results. These tests can also use a "kinetic" approach, measuring a response as a function of time can be obtained, rather than waiting for the entire reaction to complete before determining the result.

The turbidometric method is a sensitive LAL-based method used for determining endotoxin levels in a sample, with a maximum sensitivity of 0.001 EU/ml. However, for this level of sensitivity the methodology requires the use of costly, large and sensitive laboratory equipment, and therefore analysis of this type is restricted. Equipment which allows for "kinetic" LAL testing to be performed on a smaller scale, albeit with lower sensitivity is commercially available; however such systems (for example ENDOSAFE™, Charles River Laboratories) use microfluidics and optical technology to analyse the sample within a tiny sampling area. Such approaches have limited sensitivity and poor precision due to the short pathlength of the interrogating light through the sample. The resulting method will be suffer increases in analysis time and decreases in precision with a desirable reduction in sample volume that enable reductions in reagent and sample usage A quartz crystal microbalance (QCM) may be used for detecting the end-point of a gellation or agglutination reaction. For example a LAL assay can be performed by immersing the crystal within a test sample undergoing a LAL reaction. A key failing of resonating crystals is caused due to the high frequency of resonance of a pure piezoelectric resonator (for example in European Patent No 0,304,283 B1 these values are in the order of 6-12 MHz). The depth of the liquid probed by the vibration will therefore be very small, and so it is to be expected that the signal will also be very small. However, WO 2005/114138 teaches that applying a texture to the surface of a planar resonating device operating at a megahertz frequency improves the viscosity and density measuring capability. The textured surface creates an entrapped layer of liquid close to the sensor surface. In the case of monitoring of biological reactions, this not ideal because the sensor now responds according to the kinetics of the diffusion of the reagents and reaction products in the entrapped layer, rather than responding to the reaction in the bulk. In order to address these shortcomings in the devices known in the prior art, the inventors have identified that ideally a lower frequency resonator, for example of 400 kHz or less, would be optimal for the measurement of biological reactions.

U.S. Pat. No. 6,401,519 teaches how mechanical oscillators can be used to analyse the properties of fluids. Different viscosities and density values present different characteristic frequency/amplitude responses. A twin beam cantilevered tuning fork as shown in U.S. Pat. No. 6,401,519 suffers from energy losses due to moments acting at the mountings of the beams. The clamping/mounting of electrodes or coatings at the mountings of the beams will create wide variations in sensor performance. The high-loss twin beam cantilever tuning fork has little energy to resonate in liquid and is almost completely damped. Furthermore, the twin cantilevered arrangement disclosed cannot be reliably waterproofed as coating the mountings cause this to be damp the signals further.

Following extensive experimentation, the present inventors have surprisingly provided an improved apparatus and method for use in performing real time monitoring of the progress of an assay or chemical reaction, wherein the assays or chemical reaction results in a change or density or viscosity of a test sample, typically by way of the production of a gel, precipitate, coagulate, precipitate or the like. In particular, the inventors have provided an apparatus and method for the detection of endotoxin in a test sample using amoebocyte lysates, wherein the progress of the gellation of the test sample can be monitored in real time. The methods of the invention are advantageous in as far as they provide a quantitative assay result, and as such, when employed in relation to assays, such as the determination of bacterial endotoxin contamination in a sample, they provide the further associated advantages of an enhancement in sensitivity, specificity and throughput, when compared to LAL-based endotoxin tests currently known in the art.

SUMMARY OF THE INVENTION

According to a first aspect of the invention there is provided a method for the monitoring, in real-time, of a change in the viscosity and/or density of a test sample which is undergoing a chemical reaction, the method comprising the steps of:
providing a fluid test sample,
optionally adding at least one reagent to the test sample to form a test sample mixture,
immersing at least one resonant beam member of a multi-beam resonator comprising at least 3 resonating beam members in the test sample mixture, and
determining a change in viscosity and/or density of the test sample mixture by monitoring the change in at least one parameter relating to the resonance of at least one of the resonating beam members, said parameter being selected from the group consisting of; resonance frequency, quality factor and variation of the resonance phase angle of said at least one resonating beam member, and using the change in said at least one parameter to calculate the viscosity and/or density of the test sample mixture in order to determine the occurrence of a chemical reaction within the test sample mixture.

In certain embodiments, the occurrence of a chemical reaction within the test sample mixture is indicative of the presence of an analyte, contaminant, antigen or antibody within the test sample mixture. The observed increase in density and/or viscosity of the test sample mixture may be due to the occurrence of the chemical reaction resulting in at least one of a gelation, agglutination, coagulation or precipitation occurring within the test sample mixture.

In one embodiment, the step of determining the change in the viscosity and/or density of the test sample mixture by means of monitoring a change in at least one parameter selected from the group consisting of: resonance frequency, quality factor and variation of the resonance phase angle of the immersed resonant beam member(s), is performed by defining said at least one parameter relative to the same parameter as derived from at least one further resonant beam member of the triple beam resonator, said at least one further beam member also being immersed within the test sample mixture. In certain embodiments, the change in the parameter may be monitored continuously from a time point when the resonant beam member(s) is immersed in the test sample, or from when the reagent is added to the test sample to form the test sample mixture. Monitoring the parameter in this way allows the continuous, real-time monitoring of the progress of any chemical reaction which may be occurring in the test sample mixture, which results in a change in the density and/or viscosity of the sample.

In certain embodiments, the data obtained following the analysis of the at least one parameter, such as Q-factor, determined in relation to the physical resonance properties of the resonating beam members of the test strip may be processed using at least one algorithm which can be used to process this input data and determine whether a change in density and/or viscosity of the test sample is occurring. In certain embodiments, the algorithm will be stored by, and used in the calculation of output data, by an electronic processing apparatus, such as a computer.

In certain embodiments, the output parameter data relating to the at least one resonating beam member is communicated to the processing apparatus as at least one signal, which is in turn communicable to a user to indicate the presence or absence of bacterial endotoxin in the sample, due to an increase in viscosity due to gellation of test sample.

Typically, the test sample is a fluid test sample, in particular a liquid. Said liquid may be selected from the group consisting of, but not limited to: a biological sample, such as a pharmaceutical composition or a liquid for use in the same; a bodily fluid, such as blood, a blood product, or the like; or any other liquid test sample which is to be analysed for the presence of a parameter, such as a contaminant, an analyte, an antigen, an antibody or the like, wherein a change of density and/or viscosity may result in the sample during the testing process.

As herein defined, the term 'quality factor' means a unit used to measure the quality of a resonant system; specifically it is a measurement of the sharpness of resonance or frequency selectivity of a resonant vibratory system. In all resonating devices, the quality factor is affected by the surrounding environment. The quality factor of a resonant system changes according to the viscosity of the media in which it oscillates. Accordingly, as the fluid becomes more viscous, this resulting in an associated change in the quality factor of the fundamental resonance of the resonating beam structures described herein. The determination of the quality factor (Q-factor) typically allows the rate of change of the viscosity of the sample mixture to be determined.

As herein defined, the terms "resonance phase angle" relates to a measurement of the difference in phase of the resonance of one resonating beam member relative to the phase of at least one further resonating beam member, said second beam member being parallel to the first resonating beam member.

As herein defined, the term "resonance frequency" means the frequency when a material, in this case a resonating beam member of a multi-beam resonator, resonates at maximum amplitude at a specific mode of resonance. The frequency of the resonating beam will change relative to the viscosity of the fluid in which it is immersed. The invention therefore provides a multi-beam resonator viscometer device which comprises a plurality of resonating beam members, where the frequency of at least one of the vibrational resonant beam members allows a change in density and/or viscosity of a fluid in which it is immersed to be determined. The frequency of the resonating beam member as detected may not always be the resonant frequency.

In certain embodiments, the determination of the change in density and/or viscosity of the test sample mixture is performed continuously by monitoring the density and/or viscosity of the test sample mixture. Such continuous monitoring may be referred to as dynamic monitoring of the density or viscosity of the sample mixture. Accordingly, in certain embodiments, the method of this aspect of the invention allows the rate of change of density and/or viscosity of a sample mixture to be measured.

In certain embodiments, the determination of the change in density and/or viscosity of the sample mixture may be determined by the taking of a series of readings to determine the parameter of at least one of resonance frequency, resonance phase angle and/or quality factor, said readings taken at specific time points, wherein the data obtained from said readings can be analysed in order to determine, for example by calculation, any resulting change in the density and/or viscosity of the sample mixture. In certain embodiments a reading is taken every 80 seconds during the progress of the chemical reaction within the sample. In certain further embodiments, the frequency of this reading can be any valued from under 1 second to over 1 minute.

In certain embodiments, the data relating to at least one parameter which is derived from the resonance of the resonating beam member may be processed, for example, using an algorithm, in order to determine whether there has been a change in the density and/or viscosity of the sample mixture. Accordingly, in various further aspects, the invention extends to an algorithm, and further to the use of such an algorithm for processing data relating to the parameters identified hereinbefore as derivable from the resonating beam members in order to provide a numerical value which can be used in the determination of the density and/or viscosity of the test sample mixture.

In certain embodiments, the data relating to the at least one parameter which is determined from the at least one resonating beam member can be compared to known values in order to determine whether there has been an associated increase or decrease in the density and/or viscosity of the sample mixture.

In certain embodiments, an increase or decrease in the density and/or viscosity of the sample mixture can be determined by detecting a change in the resonating frequency of at least one resonating beam member of the multi-beam resonator, typically a reduction in frequency for an increase in density. In general, the determination of resonant frequency is a more direct function of density than quality factor (Q-factor) which is more related to the viscosity of the fluid.

In certain embodiments, an increase or decrease in the density and/or viscosity of the sample mixture can be determined by detecting a variation in the quality factor (Q factor), typically a decrease in the quality factor for an increase in viscosity. In certain embodiments, a measurement of the rate of change of Q factor is used to determine the rate of change of viscosity of the sample mixture.

In certain embodiments, an increase or decrease in the density and/or viscosity of the sample mixture can be determined by detecting an alteration in the resonance phase angle of at least one resonant beam member relative to at least one further resonant beam member.

Typically a change in the density and/or viscosity of the sample mixture indicates that the sample mixture is undergoing gellation, agglutination, precipitation, coagulation or the like. This change is typically caused by the reaction of the test sample with the reagent present in the sample mixture.

In certain further embodiments, the method may further comprise a step or steps to allow the resonant beam members to be calibrated. Typically calibration is performed by way of resonating the resonant beam members prior to immersion in the test sample, in a fluid which has a known density and/or viscosity, most typically air. In certain embodiments, this initial calibration step is performed prior to the test sample mixture immersing the at least one resonant beam member. In certain embodiments, this calibration includes the determination of the temperature in the environment of the multi-beam resonator. The determination of the environmental temperature can be important as this may have an effect on the speed of progression of a chemical reaction, such as a coagulation or gellation reaction. As such, in one particular embodiment, the method of this aspect of the invention further comprises the step of calibrating the multi-beam resonator prior to immersion in the test sample mixture, the calibration step comprising resonating the resonating beams in air. In certain further embodiments, the calibration step includes determining the temperature by means of determining the inner temperature within an apparatus which may house the multi-beam resonator using a thermistor or the like, and further determining the outer temperature of the environment using the multi-beam resonator, in order to establish the air temperature which the test sample will be exposed during the chemical reaction which is to be monitored by the resonant beam members of the multi-beam resonator.

In certain embodiments, the method of this aspect of the invention is an automated method, which allows for the automatic or continuous performance of the assay method.

In one embodiment, the method may be used to determine the presence and/or quantity of endotoxin which is present within a test sample, wherein this determination is based on the formation of gellation within a test sample.

Accordingly, in such an embodiment the foregoing method would provide a method for the continuous monitoring of a change in the viscosity and/or density of a test sample to determine the presence and/or quantity of bacterial endotoxin within the sample, the method comprising the steps of:

providing a test sample, admixing the test sample with a reagent comprising amebocyte lysate or a synthetic analogue thereof in order to form a test sample mixture, immersing at least one resonant beam member of a multi-beam resonator device according to the invention in the test sample mixture, and determining a change in at least one parameter associated with the resonance of at least one resonating beam member selected from the group consisting of:
- (i) the resonance frequency of the at least one resonant beam member,
- (ii) the quality factor of the at least one resonant beam member,
- (iii) changes in the resonance phase angle of the at least one resonant beam member relative to at least one further resonant beam, and using the observed change in said at least one parameter to calculate the viscosity and/or density of the test sample mixture, wherein an increase in the viscosity and/or density of the test sample mixture is indicative of the presence of endotoxin within the test sample.

In certain embodiments, the determination of the values of the identified parameters associated with the resonance of a resonant beam member within the test sample mixture are performed repeatedly and, typically continuously from the time when the reagent is added to the test sample to form the test sample mixture, or from the time point from when the resonant beam member is immersed in the test sample mixture. Monitoring the resonance of the resonant beam member in this way allows the continuous, real-time monitoring of changes of density and/or viscosity in the test sample mixture. Tracking the progress of any chemical reaction within the test sample mixture in this way is advantageous in that the method allows for the early identification of the occurrence of gellation, which can be determined by way of an increase in viscosity of the test sample mixture, in order to provide an indication that endotoxin is present within the test sample mixture.

In certain embodiments, the data obtained following the analysis of the at least one parameter, such as Q-factor, determined in relation to the physical resonance properties of the resonating beam members of the test strip may be processed using at least one algorithm which can be used to process this input data and determine whether a change in density and/or viscosity of the test sample is occurring, and whether, therefore, endotoxin is likely to be present in the test sample.

In embodiments where an algorithm is used to interpret the parameter data, this data may include for example, data relating to a parameter associated with: the frequency of oscillation of at least one of the beam members, the quality factor and/or resonance phase angle. Said algorithm can be used to provide a numerical value, which itself, or by reference to a standard derivative, can be used to determine an end point of a chemical reaction, for example of a Limulus amoebocyte lysate (LAL)-based endotoxin detection screening assay reaction, and further, which can be used to provide a quantitative measure as to whether bacterial endotoxin is present or absent from a specific test sample.

In certain embodiments, the output parameter data relating to the at least one resonating beam member is communicated to the processing apparatus as at least one signal, which is in turn communicable to a user to indicate the presence or absence of bacterial endotoxin in the sample, due to an increase in viscosity due to the gellation of test sample.

In certain embodiments, the output signal may be a visual indication which indicates the presence or absence of bacterial endotoxin in the test sample, and which may further provide a determination of the amount of bacterial endotoxin in the test sample. The indication may be a visual signal such a coloured lighting or a text or symbol based display, or an aural signal, such as a sound.

As herein defined, the term 'endotoxin' refers to potentially toxic, naturally derived compounds which are derived from pathogenic organisms, in particular bacteria. The endotoxin is therefore typically a structural component of a bacteria which is released when the bacteria is lysed. Typical examples of endotoxins include lipopolysaccaharide (LPS) and lipo-oligosaccharide (LOS) both of which are found in the outer membrane of gram-negative bacteria.

In certain embodiments, the at least one reagent which is mixed with the test sample is typically amebocyte lysate, or a synthetic analogue thereof.

In certain embodiments, the amebocyte lysate is provided in dried form, with the lysates and is reconstituted during the reaction process which occurs during the screening methods of the invention.

In certain embodiments, the amebocyte lysate may be formulated with salts and/or buffer in order to stabilise the amebocyte lysates. Performance of LAL-based endotoxin screen assays is based upon obtaining Limulus amebocyte lysates (LAL) directly from the horseshoe crab. There are four known species of the horseshoe crab, these being: Limulus polyphemus, Tachypleus gigas, Tachypleus tridentatus, and Carcinoscoypius rotuhicauda. Limulus amoebocyte lysates (LAL) is obtained by bleeding the crab and deriving the LAL from the obtained blood product. Although this procedure is rarely leads to morbidity for the crab, the associated costs of production for obtaining commercially viable quantities of LAL is high. Accordingly, alternative compounds are being developed which will replace LAL in endotoxin screening assays. Such compounds, such as synthetic analogues of LAL are within the scope of the present invention.

TAL (Tachypleus amoebocyte lysate) functions similarly to LAL in aiding the detection of gram-negative bacteria. As such, in certain embodiments of the present invention, Limulus amoebocyte lysates (LAL) may be replaced with TAL (Tachypleus amoebocyte lysate) or a synthetic analogue thereof.

Furthermore, the production of a protein by recombinant means is a technique which is widely used in the field of molecular biology. On-going work is being performed to identify the gene which encodes for Limulus amoebocyte lysates (LAL). Identification of this gene, will allow it to be cloned and expressed by recombinant means, for example, using prokaryotic or eukaryotic cells. A recombinant or synthetic form of Limulus amoebocyte lysates (LAL) or TAL (Tachypleus amoebocyte lysate) may therefore be provided. Accordingly, in certain embodiments, the invention extends to the use of a synthetic or recombinantly-derived form of Limulus amoebocyte lysates (LAL) or TAL (Tachypleus amoebocyte lysate) which may be used to replace, or to supplement the use of naturally derived Limulus amoebocyte lysates (LAL) or TAL (Tachypleus amoebocyte lysate) in the methods of the present invention.

In certain embodiments, the test sample can be selected from the group comprising of, but not limited to: a pharmaceutical composition, a biological composition or fluid, a parental preparation, such as a diluent, carrier or adjuvant for the preparation of, or for administration along with a biological or pharmaceutical composition, a reconstitution buffer or salt solution for a pharmaceutical composition or the like, an injectable pharmaceutical. In certain embodiments, the sample is a water sample, for example, sterile water, natural water, purified water, treated water or distilled water, where it is required to determine whether said water sample is free from endotoxin contamination.

The method of this aspect of the invention can also be used to follow any other assay or chemical reaction where a gel, solid, precipitate, agglutinate or coagulate is formed in a test sample as a result of a chemical reaction therein.

Accordingly, in one embodiment of the assay of the first aspect of the invention, the assay is an immunoassay, such as an enzyme linked immunosorbant assay (ELISA) which is used to detect the presence of at least one target analyte, such as an antibody or an antigen, in a test sample. In such an embodiment, the reaction between an enzyme labelled probe and a substrate can generate a precipitate. In such instances, the reagent which is added to the test sample can be an enzymatic substrate which serves to indicate whether the particular analyte is present in the test sample.

In embodiments of the invention, where the chemical reaction relates to an ELISA assay, the reagent may be Tetramethylbenzidine (TMB) (3,3',5,5'Tetramethylbenzidine) or any precipitate forming reagent, the TMB example is used for detecting horseradish peroxidase (HRP) labelled probes, such as antibodies used in an ELISA assay. This provides a convenient non-optical technique for detecting probes used in optical assays.

In a yet further embodiment of the method of the first aspect of the invention, the method may be used to monitor the progression of a latex agglutination assay where, for example, antibodies are presented on the surface of latex beads, in order to perform an antibody agglutination test. Such a test can be used to detect the presence of antigens in a reagent system. In such an embodiment, the agglutination of the antibody bound beads indicates the end-point of the assay. During the agglutination reaction, changes in the density and/or viscosity of the test sample about the resonating beams can be detected.

In a yet further embodiment, the method of this aspect of the invention can be used to detect the result of the Widal test, a presumptive serological test for Enteric fever or Undulant fever. The Widal test is widely used in developing countries to test for typhoid fever. The test demonstrates the presence of somatic (O) and flagellar (H) agglutinins to *Salmonella typhi* in the patient's serum using suspensions of O and H antigens. Typically the Widal test is performed by the tube agglutination technique. The method of the present invention could therefore be used to monitor the occurrence of agglutination in order to accurately provide a result.

In still yet further embodiments, the method of the present invention can be used to monitor the progress of other reactions which involve a chemical reaction wherein a gellation, agglutination, precipitation or a coagulation occurs within the sample mixture, or wherein a partial change of state of the sample mixture occurs, for example, during the setting of a adhesive or resin, such as an epoxy resin, wherein a first part (i.e. a reagent) is added to a second part (being equivalent to what is defined herein as a test sample) in order to monitor the setting of the composition.

In various further aspects the invention provides a multi-beam resonator which may be used to perform the methods of the invention.

Accordingly, a yet further aspect of the present invention provides a multi-beam resonator for use in monitoring a change in density and/or viscosity in a test sample, comprising:

at least 3 resonant beam members, said beam members being arranged in a substantially parallel arrangement, at least one vibratory element positioned to cause the vibration of at least one of the beam members, at least one sensor means for determining at least one parameter associated with the vibration of the resonant beam member, a reaction chamber defining a static volume, which is suitable for receiving and retaining a test sample, the reaction chamber comprising at least one inlet port to allow the introduction of the test sample and at least one outlet port of dimensions which allow for the outflow of air but not the test sample from the reaction chamber, wherein at least part of said at least one outlet port has a hydrophobic surface coating.

In certain embodiments, the resonant beam members of the multi-beam resonator are provided in a parallel arrangement and are fixed at each end of their longitudinal length to a base substrate.

In certain embodiments the at least inlet port allows the test sample to be introduced into the reaction chamber from the top of the reaction chamber. In certain embodiments at least part of the upper and lower surfaces of the at least one outlet port are coated with a hydrophilic material.

In certain embodiments, the at least one outlet port has a depth of 90 µm and a width of around 0.6 mm.

In certain embodiments, the term "monitoring a change" means continuously monitoring the progress of a chemical reaction within a test sample, but taking a plurality of readings which can be used as data to calculate whether a change in density and/or viscosity is occurring within the fluid sample. Typically the resonant beam members are placed in direct contact with the test sample which is undergoing a chemical reaction, typically by immersing the multi-beam resonator in the test sample.

In certain embodiments, the multi-beam resonator comprises 3 resonator beam members. As defined herein, a "resonant beam member" is a beam member which is part of a multi-beam resonator apparatus which is of specific dimensions and which is further comprised of a material which is suitable for resonating when immersed in a fluid sample.

In certain embodiments, the test strip comprises 2 or more vibratory beam members, typically 3, but also 5 or 7 or more vibratory beam members. Where 2 or more vibratory beam elements are used, a shearing effect is used to mediate movement of the vibratory beam member through the fluid sample. Typically said resonant beam members can be provided in a parallel arrangement and can be fixed at each end of their longitudinal length to a base substrate. In certain embodiments, at least one end of the resonating beam members may not be fixed to a base substrate. In further embodiments, the resonating beam members are defined from the same piece of material which forms the base substrate, and hence are therefore integral to the base substrate material.

Without wishing to be bound by theory, the inventors have identified that an arrangement of resonant beam members which comprises 3 resonant beam members joined at both ends confers particular advantages as the moments of the clamped ends of the resonant beam members are cancelled out. Surprisingly, this arrangement has been shown experimentally to have particular advantage when performing measurements in liquids over single ended resonating beam structures which in prior art are in general heavily damped in liquids with density greater than 1 g/ml. The benefit observed with a 3 beam resonator should also apply to multi-beam resonators comprising 5, 7, 9 or any other odd number of resonant beam members, which comprise outer resonant beam members positioned about a central beam member.

Typically the resonant beam members of the multi-beam resonator are arranged in parallel configuration, with a central beam and outer beams provided thereabout.

In certain embodiments, the central (or middle) resonating beam is of a first set of dimensions, in particular a first width and first length, while each of the further resonating beams, which are typically arranged in equal number either side of the central beam member in a parallel configuration, are of symmetrical dimensions of longitudinal length and width, along an axis defined by the longitudinal axis in the centre of the central beam.

In certain embodiments, the central resonant beam member of the multi-beam resonator has a width in the lateral dimension of 2 mm or less. In one embodiment, the width of the central resonant beam member is about 1 mm. In certain embodiments, typically the width of the central beam member is equal to the width of the outer beam members. In certain embodiments, typically the width of the central beam member is greater than the width of the outer beam members. In one embodiment, for a 3 beam resonator, the central beam is the width of the sum of the outer beam widths, said outer beam members typically being positioned parallel to the central beam member, with an equal number at each side of the central beam member.

In certain embodiments, the length of the of the resonant beam members in the longitudinal dimension can be 18 mm or less, 16 mm or less or 14 mm or less. In one embodiment, the length of the resonant beam members is 5.5 mm or less.

In certain embodiments, the distance of the spacing between resonant beam members which are arranged immediately parallel to each other is 2 mm or less. In one embodiment, the spacing between the beam members is 0.25 mm or less.

In certain embodiments the internal height of the reaction chamber is greater than 1 mm. In certain further embodiments, the internal height of the reaction chamber is less than 1 mm, so as to provide a reaction chamber with as small a volume as possible.

In certain embodiments, the distance of the spacing between the outer longitudinal lateral side of the outermost resonant beam member and the surrounding housing is 2 mm or less. In particular embodiments where the multi-beam resonator is used to make a measurement of viscosity by way of determining a change in quality factor, the dimension of the spacing between the outermost resonant beam and the surrounding housing is 0.5 mm or less. In particular embodiments where the multi-beam resonator is being used to obtain a measurement of the density of a sample fluid, through the use of a change in frequency, the distance of the spacing between the outermost lateral surface of the outermost longitudinal beam and the surrounding housing is 0.5 mm.

In certain embodiments, the distance of the spacing between the outer lateral side of the outermost resonant beam member and the innermost wall of the surrounding housing is greater than 25 μm.

In certain embodiments, the total length of the multi-beam resonator of the invention is 20 mm or less. The total length of the multi-beam resonator is typically defined by the summation of the longitudinal length of the resonant beam member and the length of the mounting zone. In certain embodiments, the length of the multi-beam resonator in the longest dimension is around 12.4 mm.

The specificity of the multi-beam resonator to the detection of density and/or viscosity of a sample may be determined by calculating the ratio of the longitudinal length of the resonant beam in view of the length of the mounting zone of the multi-beam resonator. In certain embodiments, the ratio of the beam length to mounting zone length is in the range of 1 to 9. In particular embodiments, the ratio of the longitudinal length of the beam to the length of the mounting zone is around 4.

In certain embodiments, the multi-beam resonator is configured with appropriate dimensions of resonator beam length, resonator beam width, and with a specific distance between the parallel beam members and the outer housing such that mode 1 (the first mode of vibration of the resonant beam member) and/or mode 3 (the third mode of vibration of the resonant beam member) can be used. In particular embodiments, mode 3 (the third mode of vibration) is preferred.

In a particular embodiment, the multi-beam resonator according to the present invention would comprise: 3 resonant beam members, having a longitudinal beam length of 18 mm or less, and a central beam width of 2 mm or less, wherein the distance of spacing between the 3 parallel resonant beam members is 0.75 mm or less, and wherein the ratio of the longitudinal beam length to the mounting zone is in the range of 1 to 9. In such an embodiment, the resonant beam members are typically 5.5 mm longitudinal beam length, wherein the ratio of the longitudinal beam length to the mounting zone is between 1.59 and 4.67.

Typically the resonant beam members are formed from a base substrate material. Alternatively, the resonant beam members are conjoined to a base substrate which defines part of the multi-beam resonator device, and which provides structural support in terms of strength and rigidity.

An area of the base substrate which runs substantially parallel to the resonating beam(s) may be known as a frame members, or housing. Said frame members are typically positioned parallel to either side of the outer periphery of the multi-beam resonator. In certain embodiments, the frame members are of dimensions which differ to the dimensions of the resonating beam members. In particular, the frame members can have a different longitudinal length to that of the resonating beam members, this being necessary in order to prevent stray resonances from interfering with the resonating beams, as such interference may result in a reduction in the sensitivity and specificity of the measurement of the properties of the resonating beam members when in use. In certain embodiments, the frame members are of a longitudinal length which is greater than the longitudinal length of the resonating beam members, so as to produce an amplitude-frequency peak which is at least 200 Hz lower than the amplitude-frequency peak of the resonating beams.

In certain embodiments, each resonating beam member is capable of being resonated at a frequency of between about 1 kHz to about 500 kHz.

In certain embodiments, the multi-beam resonator device may comprise a reaction chamber which receives and retains the test sample. In such an embodiment, the resonant beam members are positioned within the reaction chamber in such a way that at least one of them is immersed in the test sample when it is provided in the reaction chamber.

For the avoidance of doubt, a hydrophobic or hydrophilic coating as described herein may be substituted by a material that displays hydrophobic or hydrophilic properties or a material modified, for example but not limited to a plasma treatment, to display such properties.

In certain embodiments, at least part of the inner surface of the reaction chamber, which for the avoidance of doubt may include any of the surfaces of the resonant beam members, may be coated with a hydrophobic coating to repel a liquid test sample from being present in part of the volume of the reaction chamber.

In certain further embodiments, at least part of the inner surface of the reaction chamber, which for the avoidance of doubt may include any of the surfaces of the resonant beam members, may be coated with a hydrophilic coating which promotes the entry of a liquid test sample into the reaction chamber.

In certain further embodiments, parts of the inner surface of the reaction chamber, which for the avoidance of doubt may include any of the surface of the resonant beam members, may be coated with a hydrophilic coating which promotes a liquid test sample to enter in part of the volume of the reaction chamber and yet other parts may be coated with a hydrophobic coating to repel liquid from part of the volume of the reaction chamber.

In certain embodiments, the surface of at least part of the reaction chamber can be provided with a wettable, non-reactive coating.

In certain embodiments, the reaction chamber defines a volume. Typically this volume is static and allows a defined amount of test sample to be retained within the chamber. Retaining a set amount of sample within the reaction chamber allows a set amount of reagent to be added to the sample in order to promote the occurrence of a chemical reaction. In certain embodiments, the internal volume of the reaction chamber is equal to, or less than 1000 μl.

Typically the reaction chamber is comprised of a plurality of layers, wherein lower and upper layers define the base and lid of the reaction chamber respectively, and wherein these layers are comprised from or coated with a hydrophilic material.

In certain embodiments the reaction chamber further comprises a stainless steel layer from which the resonating beam members are defined.

In certain embodiments, the reaction chamber includes an opening above the resonating beam members that is substantially open to the reaction chamber volume, permitting for example, but not limited to, application of sample or escape of air from the reaction chamber.

In certain embodiments, a means of substantially covering the upper opening, or top of the reaction chamber volume above the resonating beam members is provided, herein and is in particular described as a reaction chamber lid structure.

In certain embodiments, a means is provided to allow entry of a test sample into the reaction chamber in the form of at least one inlet port. Typically this inlet port is provided within the reaction chamber lid structure. Typically an inlet port will be mounted above the reaction chamber to aid filling, for example by exploiting the effect of gravity.

In certain embodiments the inlet port is designed to accommodate the method of application of the test sample, for example by using a pipette whereby the dimension of the inlet port permits entry of the liquid sample, but prevent the pipette tip coming into contact with the inner surface of the reaction chamber.

In certain embodiments, the reaction chamber may be connected with at least one outlet port in order to allow air to vacate the reaction chamber upon loading of the reaction chamber with test sample. Typically an outlet port has a smaller opening area than an inlet port.

In certain embodiments at least one outlet port is provided above the reaction chamber to permit air to escape. In certain embodiments, an outlet port is positioned radially furthest from the at least one inlet port. In certain embodiments an outlet port is positioned in a corner of the reaction chamber.

In certain other embodiments, at least one outlet port is located below the resonant assembly to allow air to vacate from below the resonant assembly as the reaction chamber fills with liquid. The inventors have surprisingly identified that an outlet port positioned below the level of the sample, which is constructed such that it enables air to escape, but retains the liquid sample within the reaction chamber, can be used in the apparatus of the present invention. In a particular embodiment where a reaction chamber is constructed with an internal volume of about 60 μl with 2 outlet ports positioned below the each end of the central resonating beam members having dimensions 0.6 mm by 0.09 mm, it was surprisingly observed that no liquid sample was observed to escape from the outlet ports when the device was placed on an adsorbent surface.

In certain embodiments, the at least one outlet port is positioned to pass through at least one side wall of the reaction chamber, optimally at the lowest point above the base layer of the reaction chamber. Typically at least part of the inner surface of the outlet port may be coated with hydrophobic material. In certain embodiments, 2 outlet ports are provided, optimally positioned longitudinally below the centre resonating beam structure.

In certain embodiments, the at least one outlet port is positioned to pass through the side wall of the reaction chamber, optimally at the highest point below the reaction chamber lid. Typically at least part of the inner surface of the outlet port may be coated with hydrophobic material. In a further embodiment, 2 outlet ports are provided, optimally positioned longitudinally above the centre resonating beam structure.

The inventors have further identified that the combination of at least one of: an inlet port, an outlet port and a reaction chamber with a defined volume, permits the precise and accurate loading of a liquid sample into the reaction chamber without the need for external metering dispenser, for example by "Gilson" digital pipette. The inventors have identified that this is particularly advantageous for ensuring consistency when using the apparatus of the invention.

In certain embodiments, the resonating beam members are disposed within the reaction chamber in a position where said resonating beams(s), or more specifically the outer most portion of the most outermost resonating beam is located a defined distance from the walls which define the reaction chamber. Typically, the resonating beams are arranged such that the distance between the inner surface of the reaction chamber and the outer periphery of the resonating beams minimises the shear effect in liquid. The distance between the outer periphery of the lateral sides of the beams and the inner surface adjacent walls of the reaction chamber could be hard to control in manufacture. The inventor has identified that in certain embodiments of the invention intended to detect sub-centipoise changes in viscosity, there is no significant interaction with the outer periphery of the resonating beams to the inner walls of the reaction chamber surface where the distance is 0.5 mm or greater. In mode 3 with beams moving in opposing directions (to maximise shear), a distance between moving surfaces between the beams of 0.25 mm yields no significant increase in shear effect. This signifies that the distances required to obtain a significant shear effect between two surfaces could be much lower than 0.25 mm. In certain embodiments, the minimum distance between the outer longitudinal periphery of the resonating beams and the inner surface of the reaction chamber wall that is possible to be produced with chemical machining techniques using a 200 μm thick part is approximately 200 μm. However, finer tolerances are available with thinner materials, such as is achievable using a 100 μm thick part, which could have a 100 μm outer periphery spacing. A 20 μm thick part could have a 20 μm outer periphery of the resonating beams-inner surface features and so forth. The inventor predicts that the distance between the beams-inner surface where unwanted viscosity effects become prevalent for measurements in liquids with a centipoise value approaching water could be as low as 25 μm before the shear (tribologic) effect becomes significant.

In certain embodiments, a reaction chamber is formed around at least one resonant beam member by applying layers of water resistant material to both sides of the resonator substrate assembly, including but not limited to spacer layers, water resistant materials, joining or bonding materials, lid structures, base structures. In certain further embodiments, a reaction chamber is formed around at least one resonant beam member from laminates of polymeric materials, such as but not limited to polyester, polystyrene, PEEK, acrylic, polycarbonate or from metals such as aluminium or stainless steel. In certain further embodiments such laminates may be flat sheets, joined together to form features such as the reaction chamber. In certain further embodiments, the materials may have 3 dimensional features formed into them by techniques such as but not limited to injection moulding, thermoforming, embossing, stamping, punching, partial photo-chemical etching. A particular advantage of using such a technique may be to reduce production costs by eliminating materials or reduce variability of reaction chamber volume between multiple sensors produced.

It is well known in the art that proteins bind to surfaces that are hydrophobic, such as but not limited to polystyrene, unoxidised metal films. This is a common practise for example in the immobilisation of antibodies onto plastic microtitre plates by merely placing the proteins in contact with the surface. This is a physical adsorption process where the proteins partially denature on contact. Often additional proteins need to be added to "block" the hydrophobic surface and remove this bias from the results. The inventors have found that the use of hydrophilic materials in the resonator reaction chamber reduces the effect of physical adsorption to the reaction chamber walls. The inventors have also found that reaction chambers formed from hydrophilic materials, fill cleanly without trapping air bubble on the surface; enable simple pipetting from a single inlet to completely fill the reaction chamber in a single application without the need for an external metering dispenser (for example a "Gilson" digital pipette). In certain embodiments, materials are plasma treated to promote hydrophilic behaviour. In certain embodiments, hydrophilic materials or coatings are used as part of the reaction chamber construction. In one embodiment, materials forming part or all of the inner surface of the reaction chamber are formed from a hydrophilic material.

In certain embodiments, laminates are fixed together in a way to prevent egress of liquid from the reaction chamber, for example but not limited to adhesive bonding using pressure sensitive double sided tapes, heat activated adhesive, moisture activated bonding agent, liquid gasket.

The inventors have discovered that the height of the reaction chamber has an effect on the quality factor slope or sensitivity. In a particular embodiment where devices with a 8.5 mm beam length sensor were made into liquid sensors using spacer layers of various thickness, surprisingly it was found that a sensor with the sum of the thickness of the spacer 203 and 205 more than 0.1 mm was not damped. It is well known that the physical amplitude of a resonating assembly will be reduced with the beam length. The inventors predict in a typical embodiment of a 5.5 mm beam length, the minimum sum of spacer thicknesses will be less than 10 µm. In a further embodiment of a 14 mm beam length, a minimum sum of spacer thicknesses of 0.65 mm between the resonator and the base of the reaction chamber is required to resonate and provide a useful response. Furthermore, the inventors predict that the relationship between resonating assembly beam length and reaction chamber height will not be linear and for a resonating assembly with a beam length of 5.5 mm, a useful response will be obtained with a total reaction chamber height of 10 µm or more. Yet shorter resonating assembly beam lengths are possible and for these it is expected that lower reaction chamber height will be possible.

The inventor has identified that in embodiments of the invention which extend to the use of the apparatus or methods of the invention for detecting the occurrence of clotting, coagulation, gellation, agglutination, or precipitation or the like, within a test sample, the reaction can be made to occur in a reduced period of time under conditions wherein the surface area of the multi-beam resonator device to volume ratio of the sample is maximised. Achieving an increase in the sensing surface area to volume ratio can be achieved in a number of ways. In one embodiment, the dimensions of the reaction chamber into which the sample is placed can be varied in order to maximise the surface area of the resonator exposed to the sample. In certain further embodiments, the sensing surface area to volume ratio of the sample can be increased simply by reducing the internal volume of the reaction chamber.

In relation to embodiments of the invention which test for the presence of endotoxin within a test sample, which may typically occur upon the interaction of amebocyte lysate and endotoxin, the inventors have observed that the traditional gel-clot LAL-based analysis can take up to a time of 1 hour for gellation to occur to the sample mixture. Using the methods of the present invention, the inventors has observed that reducing the internal volume capacity of the reaction chamber, such that the amount of sample contained therein is 60 µl, can significantly reduce the gellation time for samples which are known to have endotoxin present therein.

Furthermore, the inventors predict that further reducing the volume of the sample chamber will serve to further reduce the time required for gellation. Such a principle would also apply to any other reaction wherein a gellation or similar was to occur within a test sample. For example, without being bound by theory, the inventors predicts that varying the dimensions of the reaction chamber, such that it defines an internal volume of from about 5 µl to about 10 µl would allow gellation to occur within a time period of less than 60 seconds, this being based on a sample where endotoxin was present therein. Providing screening methods wherein a quantitative result can be provided in relation to the presence or otherwise of an analyte or contaminant, such endotoxin, in a sample within 60 seconds represents a considerable, and unexpected advance over similar techniques known in the prior art.

In certain embodiments, the sample is a fluid, in particular a liquid and enters into the reaction chamber through the inlet port by means of capillarity.

In certain embodiments, at least one surface of the reaction chamber comprises a reagent which may promote the occurrence of a chemical reaction, such as, for example, amebocyte lysate or a synthetic analogue thereof in order to promote a gellation reaction in a test sample which contains endotoxin. In certain embodiments, at least part of at least one surface which defines the internal volume of the reaction chamber can be coated with a reagent, for example amebocyte lysate or a synthetic analogue thereof, in the case of an endotoxin detection assay.

In embodiments of the invention where the methods are used to determine the presence of endotoxin in a test sample, the amebocyte lysate can be dried onto a surface within the reaction chamber, using techniques such as lyophilisation. In certain embodiments, the dried amebocyte lysate can be present as a coating or deposit on at least one inner surface of the reaction chamber of the test strip or on one or more surfaces of the resonator within the reaction chamber. In embodiments, where dried amebocyte lysate is provided within the reaction chamber, typically the amebocyte lysate is reconstituted following the addition of a liquid test sample. For example, in certain embodiments, the ingress of the liquid sample into the reaction chamber results in the dried amebocyte lysate being reconstituted. Once reconstituted, the amebocyte lysate can participate in the reaction with any endotoxin present in the sample.

In certain embodiments, the reagent, such as amebocyte lysate, can be provided in a liquid solution, and can be added to the reaction chamber, prior to, simultaneously, or following the loading of the reaction chamber with the test sample. In certain embodiments, the test sample can be mixed with the reagent, such as amebocyte lysate, to form a test sample mixture prior to loading the test sample mixture into the reaction chamber.

The reagent, such as amebocyte lysate, may be coated onto a surface of the reaction chamber using any suitable coating technology which is known to the person skilled in the art, which is know for the purpose of coating at least part of a with a reagent, such as amebocyte lysate. Examples of such coating technology include, but are not limited to; screen-print, drop-deposition, dip coating and ink-jet techniques. The inventors have surprisingly discovered that the amount of reagent dispensed onto a beam can be quantified by measuring at least one parameter associated with the vibration of the resonant beam member, including frequency, amplitude, quality factor and phase in air.

Typically, the resonant beam members are composed of a material which allows them to resonate or oscillate. In certain embodiments, the material from the beam structures are substantially composed is an inert material. In certain embodiments, the resonating beam members are composed of a material selected from the group consisting of, but not limited to; silicon, alumina, aluminium, copper, palladium, iron, gold, platinum and steel. In embodiments where the beam members are comprised of steel, typically this is stainless steel.

In embodiments where the beam members are provided as an integral part of the base substrate, said beam members may be formed by a technique selected from, but not limited to; etching, in particular photochemical etching, laser treatment and mechanical punching of the base substrate. In other embodiments where beam members are not provided as an integral part of the base substrate, said beam members and base substrate may be formed by but not limited to any of the above techniques and joined together using a technique selected from but not limited to: adhesive bonding, welding, mechanical assembly, soldering.

In certain embodiments, the vibratory element which mediates oscillation of one of the beam members is a piezoelectric element. The piezoelectric element, which may also be referred to as a piezoelectric actuator, may be conjoined to at least one resonant beam member at any suitable position which can result in oscillation of the resonant beam member upon excitation of the vibratory element. The piezoelectric material can be electrically connected. Typically the piezoelectric element serves to cause oscillation of at least one of the resonant beam members, typically at a fundamental frequency of that beam member. In certain embodiments, the piezoelectric material can mediate oscillation of at least one of the resonant beam members at a harmonic frequency.

The piezoelectric material may be any suitable piezoelectric material known to the skilled person in the field, and may in particular be selected from the group comprising, but not limited to a polymer such as PVDF (polyvinylidenedifluoride), a crystal or a ceramic material. In certain further embodiments, the piezoelectric material is PZT (lead zirconate titanate). In certain embodiments, the PZT is provided in the form of a screen printed PZT actuator.

In such embodiments, the application of an electrical signal or electrical power to the piezoelectric material results in the vibration of the piezoelectric material and in turn the vibration of the conjoined resonant beam member, or of at least one beam member which is located near to the piezoelectric material in cases where the piezoelectric actuator is provided upon the base substrate as opposed to the actual resonant beam. This vibration may alternatively be referred to as actuation of the beam member.

In certain further embodiments, the vibrational movement of the beam member can be induced by magnetostriction or by direct magnetic actuation mediated by magnetic shape memory materials. Accordingly, in certain further embodiments, the vibratory element may be magnetic shape memory materials. Such materials include, for example, ferromagnetic shape memory (FSM) alloys which exhibit large changes in shape and size upon application of a magnetic field.

In certain further embodiments, vibration of the beam member may be achieved by a vibratory element which is provided in the form of a transducer which converts electrical energy into kinetic energy in the form of a resonance vibration at a specific frequency. The transducer may be connected to any suitable electrical energy source. A connecting means conjoins the transducer to the beam member allowing the kinetic energy to be transmitted from the transducer to the beam member, this resulting in vibration of the beam member.

In certain embodiments, electrical contacts and/or connections connect the vibratory element to an external control unit. These electrical connectors function to supply electrical power to the vibratory element. In certain embodiments, an insulating layer may be provided over the electrical contacts to prevent short circuiting.

Typically the vibratory element causes at least one of the beam members to resonate in a transverse direction. The phase of the resonation is a function of the vibration mode. The vibration mode can be selected by exciting the vibratory element (resonator) within a predefined frequency range. Different resonant modes are achieved by selecting a different energy state. Typically, the strongest energy state is selected, said state being out of phase by exciting the resonant beam at a particular frequency. In certain embodiments, the beam members of the test strip can be excited by the use of pink noise, white noise, a chirp or the like. This can, in certain embodiments, then be used as basis to determine the resonant mode 1, resonant mode 3 or any other useful mode of the resonant beam member. In alternative embodiments, the Q-factor can measured the response resulting from excitation the chirp, pink noise or white noise response. In certain further embodiments, closed loop oscillation of the at least one resonant beam member may be used. In certain other embodiments chirp, pink noise or white noise can be used to generate a signal from which the resonating beams can be calibrated.

In certain embodiments, oscillation of a resonant beam member can be detected by a sensor means or sensor element. In a particular embodiment, where a vibratory element is attached to at least one resonant beam member of the multi-beam resonator device, the sensor means is conjoined to a different resonant beam member. In certain embodiments, where a vibratory element is attached to at least one resonant beam member of the multi-beam resonator device, the sensor means is conjoined to the opposite end of the same resonant beam member. In embodiments where the vibratory element is conjoined to the base substrate, as opposed to a specific resonant beam member, the sensor element may be conjoined to a resonant beam member, or alternatively, may be applied to the base substrate, in the proximity of the resonant beam members. In further embodiments, a plurality of sensor means may be used. Said plurality of sensor means may be applied to different beam members, to the base substrate or to both the resonating beam members and further to the base substrate.

In embodiments where the sensor means is applied to the base substrate, typically said sensor is applied to an area which is proximal to the end of the length of the beam member. Typically, the sensor means is conjoined to the beam member in proximity to the end of the beam members, but at a longitudinal end opposite to that where the vibratory element is provided. This spatial separation of the vibratory element and the sensor element (which may also be achieved by conjoining the vibratory element and the sensor element to different beam members) ensures that the sensor detects only oscillation of the beam member, and is not influenced directly by the vibration which is being emitted from the vibratory element.

In certain embodiments, the sensor means is a piezoelectric member, or substantially comprised of a piezoelectric material. This piezoelectric element serves to detect and convert the physical movement of the beam member to which it is conjoined into a measurable signal. The sensor means may further have electrical connectors conjoined thereto, in order that an output signal can be sent to a unit which can use the output signal as a measurable signal in order that the oscillation of at least one of the associated beam members can be determined.

Typically, the sensor means for determining the frequency of oscillation of at least one of the beam members is conjoined directly to a beam member. Generally, said beam member is also directly conjoined to a vibratory element. In certain embodiments wherein there are 3 or more beam members, sensor means for determining the frequency of oscillation may be conjoined to more than one of said beam members, said beam members typically being a beam member which does not have a vibratory element conjoined thereto. Typically however, both the vibratory means and the sensor means are attached to the same beam member, with these being spaced at either ends of the beam member.

In certain embodiments, electrical contacts and/or connections connect the sensor means for determining the frequency of oscillation to an external control unit. Typically the piezoelectric actuator and piezoelectric sensor elements and electrical connections thereto are insulated from the sample fluid which is present in the reaction chamber.

In various further aspects of the invention, there is provided a test strip which comprises the multi-beam resonator device of the invention. Such a test strip can be used for the automated analysis of the density and/or viscosity of a test sample.

As such, a yet further aspect of the invention provides a test strip comprising multi-beam resonator device as herein defined, for use in the quantification of the occurrence and progress of a chemical reaction within a test sample, by means of monitoring a change in the viscosity and/or density of a test sample which is undergoing a chemical reaction, after a defined period of time wherein said chemical reaction may result in the gellation, agglutination, precipitation or coagulation or the like of the test sample.

As such, a yet further aspect of the invention provides a test strip comprising multi-beam resonator device as herein defined, for use in the continuous, real-time monitoring of the occurrence and progress of a chemical reaction within a test sample, by means of monitoring a change in the viscosity and/or density of a test sample which is undergoing a chemical reaction, wherein said chemical reaction may result in the gellation, agglutination, precipitation or coagulation or the like of the test sample.

In various further aspects, the present invention extends to the use of the foregoing methods and apparatus in methods for monitoring the progress of assay methods and chemical reactions, by way of monitoring a change, or otherwise, of the density and/or viscosity of a test sample.

Accordingly, a further aspect of the invention provides for the use of a method as hereinbefore described for the continuous monitoring of a test sample in order to determine a change in the viscosity and/or density of the test sample, wherein the sample is, or may be, undergoing a chemical reaction.

In certain embodiments, the method may be used for the detection and/or quantification of a contaminant, such as bacterial endotoxin, in a test sample, said test sample typically being a fluid sample.

In certain further embodiments, there is provided the use of a method according to the invention for monitoring a change in the density and/or viscosity of a test sample, wherein said test sample may be used in an immunoassay, such as an ELISA, or in an agglutination assay, or in an assay to determine coagulation of the test sample.

A yet further aspect of the invention provides for the use of a multi-beam sensor apparatus, as hereinbefore describe, for use in determining the density and/or viscosity of a test sample, wherein the sample is, or may be, undergoing a chemical reaction.

In certain embodiments, the test sample is a test sample which is to undergo a coagulation reaction, an immunoassay, such as an ELISA, or an agglutination reaction.

In certain further aspects, the invention extends to the use of the test strip of the present invention in the continuous monitoring of a change in the viscosity and/or density of a test sample which is undergoing a chemical reaction wherein the chemical reaction results in the formation of a gellation, agglutination, coagulation or precipitation product or the like. In certain embodiments, such a chemical reaction relates to the formation of a gel during the performance of an endotoxin detection assay, such as a *Limulus* amoebocyte lysates (LAL)-based endotoxin screening assay. In certain further embodiments, the chemical reaction is that which occurs during the performance of an immunoassay, such as an ELISA assay. In further embodiments, the chemical reaction is that which occurs during a coagulation assay, such as the determination of coagulation time as part of a prothrombin test. In certain further embodiments, the chemical reaction relates to the formation of agglutination complexes during a latex agglutination assay, or similar According to a yet further aspect of the invention there is provided a kit for use in monitoring a change in the viscosity and/or density of a test sample through the determination of at least one data value which is derived from a resonant beam member which is caused to resonate within the test sample, said data parameter being used to calculate the density and/or viscosity of the test sample in order to determine whether the test sample is undergoing a chemical reaction, the kit comprising a test strip according to the invention along with instructions for the use of the same and the provision of appropriate reagents.

In certain embodiments, the occurrence of the chemical reaction within the sample mixture results in the formation of a gellation, agglutination, coagulation or precipitation product or the like within the sample mixture.

According to a yet further aspect of the invention, there is provided a test kit for detecting bacterial endotoxin, said kit comprising:

a test strip comprising at least 3 resonant beam members which are provided within a reaction chamber having a defined internal volume and which is suitable to receive and retain a test sample, a reagent comprising amebocyte lysate or a synthetic analogue thereof, means for causing at least one of the resonant beam members to resonate and means to detect the resonation of at least one of the resonant beam members, and instructions for the use of the same.

In certain embodiments, said kit further comprises apparatus and/or instruments for performance of the method which are sterilised such that they are free from endotoxin contamination.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "a resonant beam member" includes a single resonant beam member as well a two or more different resonant beam members.

BRIEF DESCRIPTION OF THE DRAWINGS

FIG. 1 shows a representation of a test strip and a test meter and the stepwise process used to calibrate the test meter and confirm the viability of the test strip (FIG. 1(a)), the loading of the sample to be tested onto the test strip (FIG. 1(b)), and the engagement of the loaded test strip with the test meter in order to allow analysis of the test sample, and the provision of an associated reading (FIG. 1(c)), FIG. 2 shows a schematic representation of a test strip (FIG. 2(a)) as well as an exploded version of said test strip (FIG. 2(b)), FIG. 6 shows the parameters of the triple beam resonator which were varied in order to assesses the correlation of sensor dimensions to viscosity and density measurement sensitivity, FIGS. 7 (a) to (f) show a series of tables illustrating the dimensions of 6 different families of triple beam resonators, FIG. 8 (a) shows the FEA for a triple beam resonator design (cell 2 DOE) at mode 1 at 16,436 Hz, while FIG. 24(b) shows the triple beam resonator (cell 2 DOE) at mode 3 at 18,347 Hz.

FIG. 15 is a table showing the dimensions of the triple beam resonators as well as their results in terms of viscosity and density sensitivity, the designs listed correlate with the sensors detailed in FIG. 7, for example Cell 15 DOE is the same as design 15 as detailed in FIG. 15, FIG. 23(a) shows a response peak of a 0.1 EU/ml endotoxin sample. Response curves were taken at 80 second intervals.

FIG. 23(b) shows the response peaks of a 0 EU/ml endotoxin sample. Response curves were taken at 80 second intervals.

Figure 3B:
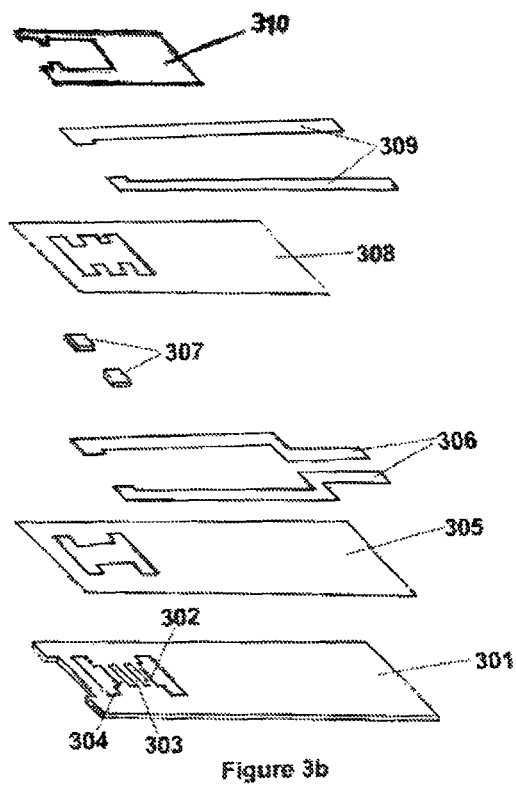
FIG. 3 shows an alternative embodiment of a resonant assembly which may be used in the method of the invention (FIG. 3(a)), along with an exploded view thereof (FIG. 3(b))

The present invention will now be described with reference to the following examples which are provided for the purpose of illustration and are not intended to be construed as being limiting on the present invention.

DETAILED DESCRIPTION OF THE INVENTION

The present invention provides an improved apparatus method for the real time measurement of assays and chemical reactions wherein a change in viscosity and/or density, by for example, gellation, precipitation, agglutination or coagulation, occurs.

Without wishing to be bound by theory, the inventors have surprisingly identified that multi-resonator beam devices, such as triple beam resonator devices, exhibit high levels of sensitivity to both viscosity and density of a fluid test sample. This sensitivity allows for high accurate readings to be obtained, which can be obtained in a very short, and ongoing, period of time. This therefore allows the on-going monitoring of a chemical reaction within a test sample, in order to track its progress.

Following extensive experimentation, the inventors have identified that the preferential mode of the double-ended triple-beamed resonating viscometers provided by the invention in liquid is mode 3. The use of a triple beam embodiment of the multi-beam resonator device in mode 3 provides particular benefits such as (i) that the centre beam moves in anti-phase to the outer beams, providing maximum shear of the fluid being sampled, conferring superior viscosity sensitivity compared to other resonators, (ii) that the moments at the beam ends are cancelled, ensuring superior signal gain which potentially provides larger dynamic range than other types of resonating sensor for fluid viscosity sensing and (iii) the net mass movement at all time is zero, resulting in a sensor that requires low power to drive, such as that afforded by printed film PZT or PVDF film, yet produces a large gain that can be easily read by simple and inexpensive electronics.

Furthermore, with regard to the 6 edges of the respective 3 beams gliding through the liquid, the observed high level of energy efficiency provides high sensitivity to viscosity changes in the surrounding test sample. Such sensitivity has been identified by the inventors as being particularly suitable for monitoring the small changes seen in viscosity and density which occur during chemical, reactions. This is coupled with the ability to monitor the progress of the biological reaction in a rapid and on-going manner in order to provide a novel, field leading approach to assay monitoring.

Furthermore, with regard to the double ended triple beam arrangement, the inventors found that the highly efficient resonating structure particularly suitable for providing a readily measurable output in a wide range of viscous liquids, ranging from that of water to a blood clot. Such a wide dynamic range has been identified by the inventors as being particularly useful for monitoring reactions where the initial state of the reaction mixture is water-like and the end-point is a gel.

Without wishing to be bound by theory, the inventors have identified that the double-ended triple-beamed embodiment of the multi-beam resonator (which may also be referred to as the multi-beam viscometer, or multi-beam microviscometer) provides a highly sensitive viscosity measure with a signal that is strong enough to be readily and easily quantified without complex models using low-cost and portable equipment. For example, and again without wishing to be bound by theory, the inventors have identified that the triple beam resonator devices of the invention provide a response which can be on average up to 60 decibels above the signal noise, this offering hundredths of a centipoise sensitivity.

Furthermore, the triple beam resonator devices of the invention require only a single pair of actuator/receiver elements, situated on one of the beams to obtain a single peak due to an anti-phase resonance. This differs significantly to single ended tuning forks that need moment cancelling actuation or, or double-ended twin-beamed devices that require phase controls. This arrangement as applied to the triple beam resonator of the invention removes the need for such complex drive electronics and allows for significant simplification and miniaturisation of circuitry and interconnections.

Without wishing to be bound by theory, the inventors have further identified, that in certain embodiments, the double-ended triple-beam resonator of the invention produce an improved technical effect when measuring assays as the resonator probes at least 50 µm of the liquid test sample located on either side of the resonating beam members. No labels, probes or "beads" are required to facilitate the obtaining of a test result. The arrangement of the beams within the double-ended triple-beam resonator of the invention places the resonating portion at the centre of the reaction, this further helping to achieve maximum sensing effect.

Another key benefit of the resonator device assembly of the invention is the temperature-frequency bias. Vibration based viscometers known in the art, such as that disclosed in U.S. Pat. No. 5,211,054, provide an output signal which is greatly dependent upon temperature. The double-ended triple-beam resonator device of the invention is affected by only minimal temperature to signal output deviations. Such derivations have in fact been identified as being predictable, hence they can be taken into account when analysis any results produced.

The multi-beam resonator devices of the invention can be easily waterproofed and therefore can be electrically insulated, such that they have improved functionality when used with fluids having high dielectric constants. Resonant sensors known in the prior art are typically damped at the mountings, such that a waterproof coating is not typically used. If a coating is used, this must be kept thin, possibly as this as 100 nm, however capacitance coupling between the electrodes and the liquid occurs and drowns the resonant response. This does not occur with the multi-beam resonators of the present invention, and as such layers as thick as 100 um can be applied without damping the resonance.

Due to these properties, the apparatus and methods of the invention may have particular application in such diverse areas as haematology, biochemistry, immunology, microbiology, DNA analysis, protein crystallisation, cell cultures and more generally in any high throughput screening technique, or assay method, such as an immunoassay, which is used for the detection of a contaminant, analyte, antigen or antibody in a test sample.

In one application, the apparatus and methods of the invention may have particular utility in assays for detecting endotoxin contamination of samples, and in particular fluid samples. The present invention uses a multi-beam resonating sensor to provide a quantitative analysis of a LAL assay. The detection of at least one of a number of parameters associated with the oscillation of a resonating beam member which is provided by the multi-beam resonating sensor allows for the dynamic monitoring to determine the occurrence and progression of a gellation-like clotting reaction which occurs following the exposure of horseshoe crab amebocyte lysate to endotoxin.

The double-ended triple-beam viscometer of the invention not only provides a highly sensitive, real-time measurement of the on-going LAL based gellation reaction, but also provides a significant advance over LAL-based analytical methods known in the prior art, as the present methods and apparatus do not require a waiting time to allow the gelation reaction to occur before the results can be obtained, Rather, apparatus and methods of the present invention can monitor the progress of the reaction immediately due to the high sensitivity, hence it is not necessary to wait for the gellation reaction to advanced to a stage where there is entrapment of particles in order to obtain an assay result. This important advance allows the provision of an endotoxin test method and apparatus with a 2 minute response time. This should be compared to the 1 hour test provided by assay methods of the prior art, such as that described in U.S. Pat. No. 5,211,054 as discussed hereinbefore.

In one embodiment of the invention, there is provided a sensitive, yet robust testing kit which can be used in applications where the LAL gel-clot based method would normally be used, for example in the testing of dialysate solutions, or for parental testing.

A test strip component, which may be disposable, contains the multi-beam resonating sensor and any required reagents. The test strip component would be used in conjunction with a metering device or a reader apparatus which would interact with the test strip such that at least one parameter of the resonating beam members, such as frequency, quality factor or resonance phase angle can be determined.

An arrangement of such a test strip and reader apparatus is shown in FIG. 1. Specifically, FIG. 1(a) shows a disposable test strip 100, which has been removed from its protective enclosure and which is ready for use. The test strip is orientated into a position which makes it ready for insertion in the test meter 101.

Once inserted the resonator would be excited and the resonances measured using a standard frequency analyser as anyone skilled in the art would know. For example, the document of Green (Publicly disclosed undergraduate Thesis. Brunel University, 1995) teaches that the frequency of resonance in vacuum, air or liquid can be found and monitoring using either an open-loop or closed-loop method. An open-loop method is where frequency is scanned between a pre-defined range, for example using a Solatron 1220 Frequency Analyser. A closed-loop method is where the frequency is scanned from DC until a resonant signal is detected. The circuit then locks onto the signal and tracks any changes by using the output signal from the pickup. As the measurement changes, the beam with the pickup resonates at a slightly different frequency from the forced frequency. Part of this signal is corrected for the 90 degree phase shift between the beams and fed back to the first beam forcing the vibration frequency, thus the circuit is self-tracking, automatically detecting changes in resonant frequency. For example, an Apollo Universal Counter Timer could be used for this approach along with a suitable power supply.

Upon inserting the sensor into the reader apparatus, a frequency spectrum depicting the frequency of resonance of the resonating beams present in the multiple beam resonator sensor would be obtained, with this frequency determining the resonating of the beams in air. More specifically, this measurement is achieved by exciting the piezoelectric actuator with a range of frequencies and recording the resulting amplitudes of the resonance of the resonating beam members of the device.

The frequency of the different resonant modes and the shape of the "peaks" would be used to calibrate the test strip and would also be used to validate or self-check the multibeam resonating sensor before use. This calibration step may be particularly required if the test strip has previously been used to test a previous sample, as this calibration step will determine whether any sample has been retained in the reaction chamber of the test strip from the previous use.

If the sensor passes the initial calibration and validation test protocol, the display 102 on the test meter 101 will prompt the user to add the sample liquid to the reaction chamber of the test strip. FIG. 1(b) shows the application of a liquid sample to the sample entry window 103 on the test strip. Typically the liquid sample uses capillarity to enter into the reaction chamber of the test strip. FIG. 1(c) depicts the reader apparatus meter 101 showing the result of the assay, this result being directly linked to whether a change in viscosity due to the gellation reaction has resulted in the sample.

On completion of the assay, the change in viscosity determined by analysis of the resonant frequency spectrum and the amplitude of nodes less favoured by the resonant beam assembly being surrounded by a gel clot is compared with a known set of data stored within the meter (the calibration curve).

FIG. 2 shows a further embodiment of a test strip for use in the present invention. FIG. 2(a) shows a schematic of a disposable test strip 200. FIG. 2(b) shows an exploded schematic of the disposable test strip 200 shown in FIG. 2(a). The disposable test strip 200 comprises a base substrate layer 201 onto which a reagent layer 202 is disposed. Alternatively, the reagent layer 202 may be provided as a coating which is disposed upon a part or the whole of any internal surface of the reaction chamber. A first reaction chamber forming layer 203 is provided upon the base substrate 201. This reaction chamber forming layer may be formed using a pressure sensitive double sided adhesive tape, punched or cut or by application of screen printing or ink jet printing. Additionally outlet ports 210 may be formed as part of the layer. A second reaction chamber forming layer 205 may be additionally laminated over the first reaction chamber forming layer to provide further reaction chamber height, and may be formed using a patterned pre-cast film, or by application of a screening printing or ink jet printing technique or through the use of a suitable non-reactive polymeric material.

A resonant assembly 204 comprising a plurality of resonating beams, in this case 3, may be laminated over the first reaction chamber forming layer. Additionally, a mechanical spacer, 206 may be included to ensure even lamination of subsequent layers. A further reaction chamber forming layer 207 is disposed upon the resonant assembly 204. A final reaction chamber forming layer 208 is disposed upon the previous reaction chamber forming layer to permit the inclusion of further outlet ports 211 in the upper part of the reaction chamber. Lastly, a polymeric film 209 is laminated onto the top surface of the upper reaction chamber forming layer 208. The polymeric film 209 provides an upper lid on the reaction vessel which protects the underlying structures of the test strip from mechanical damage. The polymeric film 209 also serves to improve the stiffness of the test strip, particularly where the test strip is in an embodiment where it is disposable. Additionally disposed upon the polymeric film, may be features including an inlet port 213 and an outlet port 212.

Alternatively, the first and second reaction chamber forming layers 203 and 205 may be combined where suitable dimensional and material selection permits, as may the third and fourth reaction chamber forming layers 207 and 208. Furthermore mechanical spacer 206 may be incorporated as part of resonator 204 if required. Alternative materials may permit further combinations of elements, for example embossing of polymeric material to form a combined base substrate 201 with first and second spacer layers 203 and 205.

Figure 3A:

FIG. 3 shows an embodiment of a multi-beam resonator structure which is suitable for measuring properties such as the density and viscosity of a test sample, in particular a body fluid, before and during a chemical reaction. As shown in FIG. 3(a), there is provided a triple beam resonator sensor assembly 300 for integration into a disposable test strip sensor device of the invention.

FIG. 3(b) shows an exploded schematic of a triple beam resonant sensor assembly for integration into a disposable test strip. A base substrate 301 is patterned with three resonant beam structures 302, 303, and 304. These beam structures may be formed by any conventional method such as laser or chemical etching or by stamping of the base substrate. A patterned insulating dielectric layer 305 is disposed onto the base substrate 301. The patterned insulating dielectric layer may be disposed thereon by any conventional method such as screen printing or ink jet printing. Alternatively, a pre-cast film may be laminated over the base substrate 301.

Patterned conductive tracks 306 are disposed on the patterned insulating dielectric layer 305. These conductive tracks may be disposed by any conventional method such as screen printing or ink jet printing and can be composed of any suitably conductive and chemically inert material.

A pair of piezoelectric elements 307 are disposed onto the patterned conductive tracks 306, at a location which is in close proximity to the central resonant beam 303. A second patterned insulating dielectric layer 308 is disposed to cover the majority of the patterned conductive tracks 306. The second dielectric layer 308 is shorter in length at the end distal to the beams in order to expose the ends of the conductive tracks 306. The second patterned insulating dielectric layer 308 may be disposed by any conventional method such as, but not limited to screen printing or ink jet printing. The second patterned insulating dielectric layer 308 functions to cover the conductive tracks 306 in order to allow the printing of a further conductive track (shown in this embodiment as feature 309) upon this layer. Accordingly, a second set of patterned conductive tracks 309 are disposed over the second patterned insulating dielectric layer 308 and the piezoelectric elements.

The patterned conductive tracks 306 and 309 may run the length of the base substrate 301, as shown in FIG. 3(a), such that an electrical connection can be made between the piezoelectric elements 307 and an external device, such as a meter, by means of any suitable connector (not shown).

A thick polymeric waterproof layer 310 covers the tracks and electrodes and prevents short circuiting and liquid impedance interference when the device is immersed in water.

Figure 4:
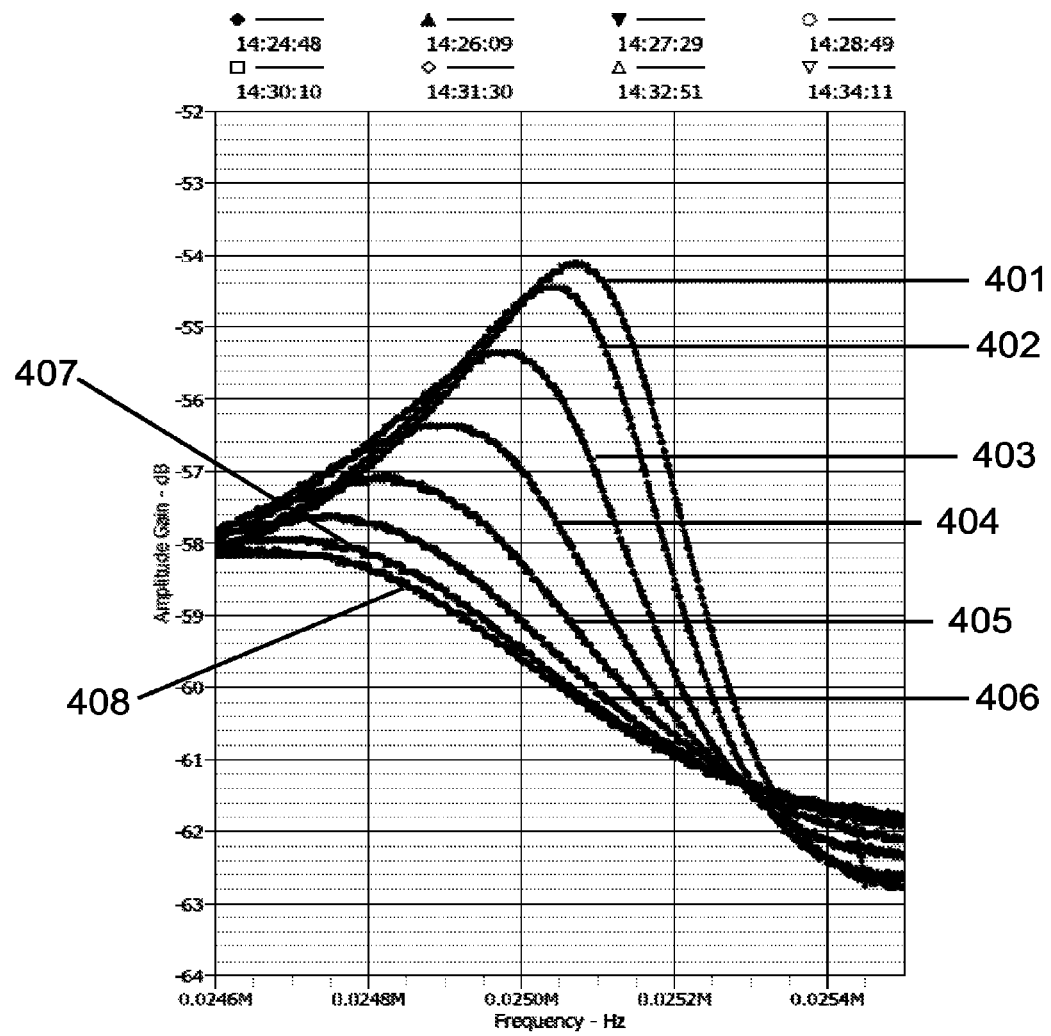
FIG. 4 shows a typical triple beam resonator sensor response to a gellation or coagulation reaction: this shows a LAL and Endotoxin (10 EU/ml) reaction.

FIG. 4 is a graph illustrating a typical resonant sensor frequency response to a gellation or coagulation reaction. Trace 401 provides the amplitude vs. frequency response with the resonant sensor dipped in un-reacted reaction mixture. The resonant mode with a peak at approximately 25.1 kHz changes due to viscosity. In a low viscosity fluid, in this case un-reacted reaction mixture, the sensor resonates over a small range of frequencies, the quality factor or Q factor (the spread of frequencies associated with a peak at ½ peak height) is high. Traces 402 to 408 provide the amplitude vs. frequency response with the resonant sensor dipped in a reaction mixture undergoing coagulating or a gellation reaction, at one and a half minute intervals. As the solution undergoes reaction (that eventually forms a thin and watery gel in one hour at 37° C.), the peak disappears and the Q factor decreases. The changing solution between the shearing beams changes the nature of the resonance. This appears as a significant decrease in amplitude shown in the series 402 to 408. This response allows for the determination of the viscosity of the gellation mixture at the start, during and at the end of the reaction. It is also possible to determine the rate at which the fluid mixture gels. Both of these are used to indicate the level of endotoxin contamination in the sample.

Figure 5:
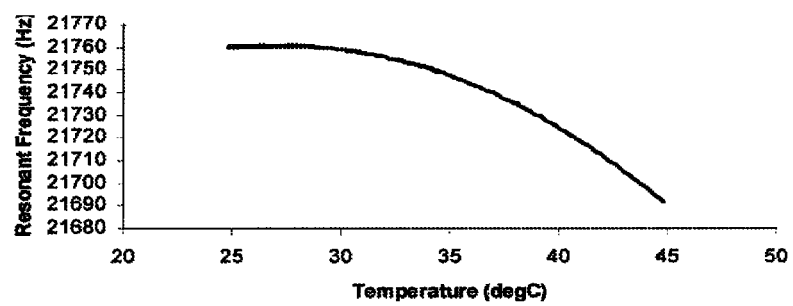
FIG. 5 shows a typical triple beam resonator sensor frequency response to temperature.

FIG. 5 shows a typical resonant sensor response with respect to temperature. This relationship is used both to check that the sensor has been equilibrated/calibrated to the correct temperature and to ensure that it has been manufactured to specification, by comparing the position of a particular resonant peak with its expected position at the temperature of the test strip as measured by the test meter. On insertion of the test strip into the test meter apparatus, the test meter is switched on either by the presence of the test strip breaking a light beam, by depressing a micro-switch, or by engaging with an electrical contact which connect the piezoelectric components to the edge of the test strip. Within the meter 101, and close to the test strip connector port, is a temperature measuring device, either a thermocouple or a thermistor. This measures the temperature in the vicinity of the test strip. This temperature reading is used with the frequency response in air to decide whether the sensor is equilibrated and at the correct temperature.

The multiple beam (multi-beam) resonating sensor of the invention confers a number of advantages over the amebocyte lysate based methods which are used in the prior art for the detection of endotoxin, including; (i) thermal stability, wherein the frequency response to a sample temperature is a small contribution to the signal. (ii) sensitivity, where the resonant beam is more sensitive to gellation that a quartz crystal microbalance (QCM) device, such that lower reagent concentrations are needed to obtain a result. Viscosity sensitivity is inversely proportional to fundamental frequency. As such, QCM devices operate in MHz domain, whilst the resonant devices described here operate in the kHz frequency range. (iii) Manufacturing, as the resonant beam sensor is made from low cost materials, for example steel rather than polished solid crystals. (iv) Liquid volumes, because, as piezocrystals become small they become difficult to handle and the signal bias effects due to clamping forces increase. Double-ended resonators resonating do not suffer from this issue as the clamping forces are cancelled at each end. QCM crystals need to be placed in housing such that the liquid meniscus has to be an angle to the mounted crystal. This eliminates reflections from the surface of the liquid bouncing back to the crystal surface. (iv) Electrodes. The electronic components in the QCM define the sensing area. The electrodes are in contact with the sample, so coatings are needed. In a resonant beam the electronics are mounted away from the liquid retaining reaction chamber. Triple beam resonators do not need to be mounted at any specific angle.

EXAMPLES

Example 1

A Method Used for a Sensor Manufacture

Sensor Manufacture

The multi-beam resonating sensor, which in this embodiment is a triple beam resonator comprised of 3 resonating beam members arranged in a parallel configuration, is comprised of the following materials: (i) Steel of 200 μm thickness supplied from Precision Micro Ltd (Birmingham, UK), (ii) Insulation 4924 (ESL, King of Prussia), (iii) Gold Cermet Ink 8836 (ESL, King of Prussia), (iv) PZT paste (Highland BioSciences Limited, Inverness, UK), (v) Silver Palladium Ink 9912-K (ESL, King of Prussia), (vi) Insulating Dielectric 240-SB (ESL, King of Prussia), (vii) Polystyrene Film, AR9020 (Adhesives Research, Ireland), (viii) Acrylic Adhesive Tape (Adhesives Research, Ireland), (ix) Hydrophilic Film 9971 (3M, Minneapolis, USA), and (x) Medical Grade Polyester (Autotype, Oxon, UK)

The multi-beam resonating sensor fabrication procedure was as detailed as follows: Triple beam resonating sensors were patterned into the sheet steel using a standard photoetching process. The additional components required to drive the resonator were deposited onto the sheet steel base substrate using a thick film process. Insulation 4924 was deposited in such a way as to prevent the conductive tracks of the top and bottom electrodes from short circuiting. The base electrode for the PZT components was printed on top of the insulation using a gold compound 8836. A PZT paste was printed at the ends of the beams. A further gold electrode was printed over the top of the PZT to provide an electrical connection. A silver-palladium track was created using compound 9912-K to connect the gold electrodes to the edge of the sensor enabling push-fit insertion into a "meter" instrument. The pastes were allowed to level, dried and fired as described in the manufacturer's specification. A rubberised waterproofing layer 240SB preventing liquid coming into contact with the electrodes, preventing liquid impedance from becoming a confounding signal.

The devices were polled by applying in excess of 100V DC current to the electrodes attached to the PZT, whilst the devices were heated to the curie temperature at above 200° C.

The insulated sensors were fitted with a flow cell constructed from laminated tapes. A layer of double sided tape was patterned to leave the beams unhindered, and was used to form a spacer layer between the base of the sensor and a sheet of polyester. A similar patterned piece double sided tape such as was placed on the top surface of the sensor. A final piece of patterned polyester film was used to create a well. To prevent evaporation of the test sample, a piece of 9971 hydrophilic coated polyester was sealed over the reaction chamber.

Example 2

Optimisation of Triple Beam Resonator Structure and Dimensions

This example was performed in order to determine the optimal configuration of the triple beam resonator in relation to its sensitivity in use for detecting viscosity and density in a liquid rest sample. This analysis also allowed the identification of the most influential aspects of triple beam resonator design, which enable the real time monitoring of assays and chemical reactions where precipitation, agglutination, gellation or coagulation is a measurable parameter which indicates the occurrence or progression of a chemical reaction.

(i) Triple Beam Resonator Design

Figure 6:
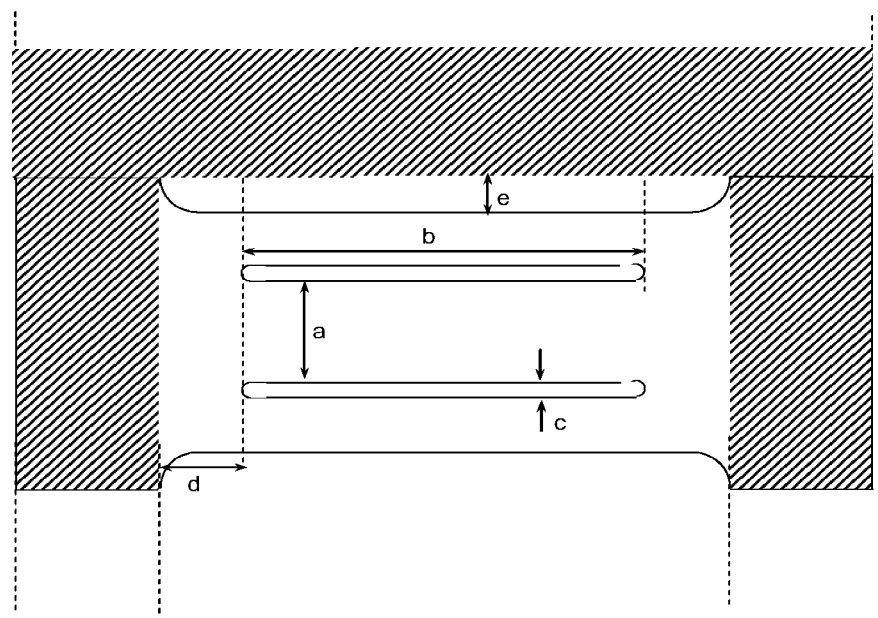

FIG. 6 shows the parameters of the triple beam resonator which were varied in the performance of this experiment. In this figure, (a) relates to the width of the middle (central) beam of the resonating beam members, (b) relates to the beam length, (c) relates to the spacing distance between beams, (d) is the beam mounting zone, and (e) is a gap between the outer beam and the device housing. The outer beam widths (not marked) are of equal width and equal to 50% of the width of the central beam as described in (a). FIGS. 7 (a) to (f) show tables illustrating the specific reaction chamber dimensions of 6 groups of triple beam resonators comprising 48 individual triple beam resonators (named Cell 1 DOE through to Cell 48 DOE) which were produced for testing in this example. The dimensions shows are all in millimeters. Families of designs were made and grouped according to the ratio of beam length to beam mounting zone length. Within the family groups, other parameters including gap to frame and gap between beams were varied to allow investigation of potential interaction of parameters.

When constructing the various triple beam resonators, the standard dimensions shown in Table 1 were typically used. The low, middle and high setting values which are shown relate to a lowest and highest setting, in addition to centre points (or middle setting) for each parameter. These values are then used as part of the experimental design.

TABLE 1 standard dimensions (in millimetres) of features of the beam members of the test triple resonators

| | Low Setting | Middle Setting | High Setting |
| --- | --- | --- | --- |
| Beam length | 5.5 mm | 7 mm | 8.5 mm |
| Beam width (centre) | 1 mm | — | 2 mm |
| Overall length | 8.5 mm | 10.45 mm | 12.4 mm |
| Gap between beams | 0.25 mm | 0.5 mm | 0.75 mm |
| Gap to frame | 0.5 mm | 1 mm | 2 mm |

Figure 8A:
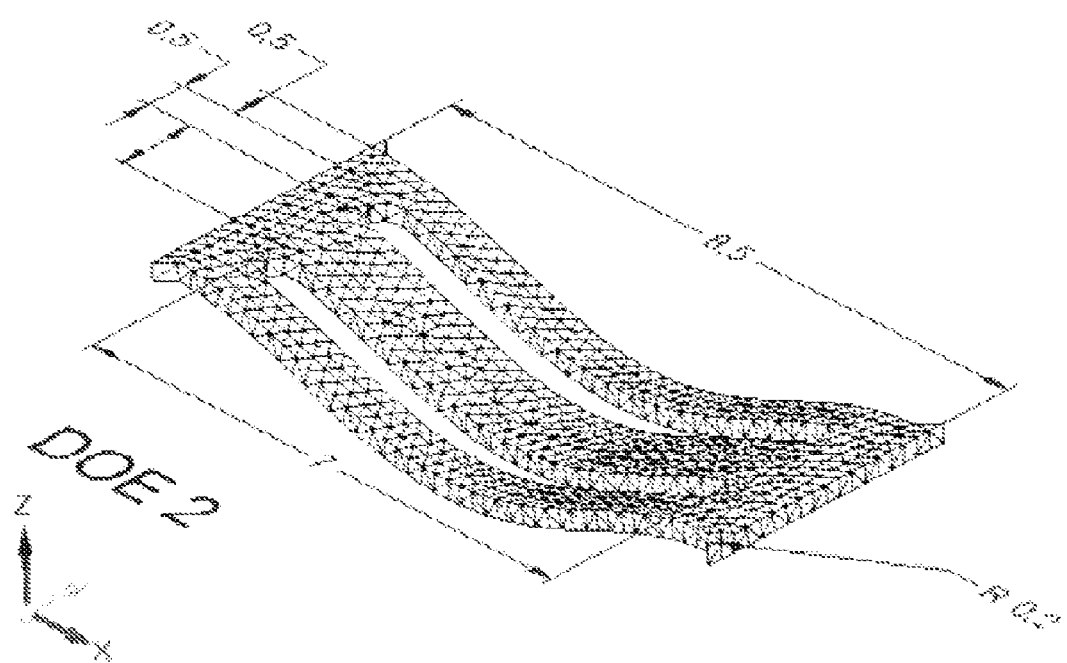
Figure 8B:
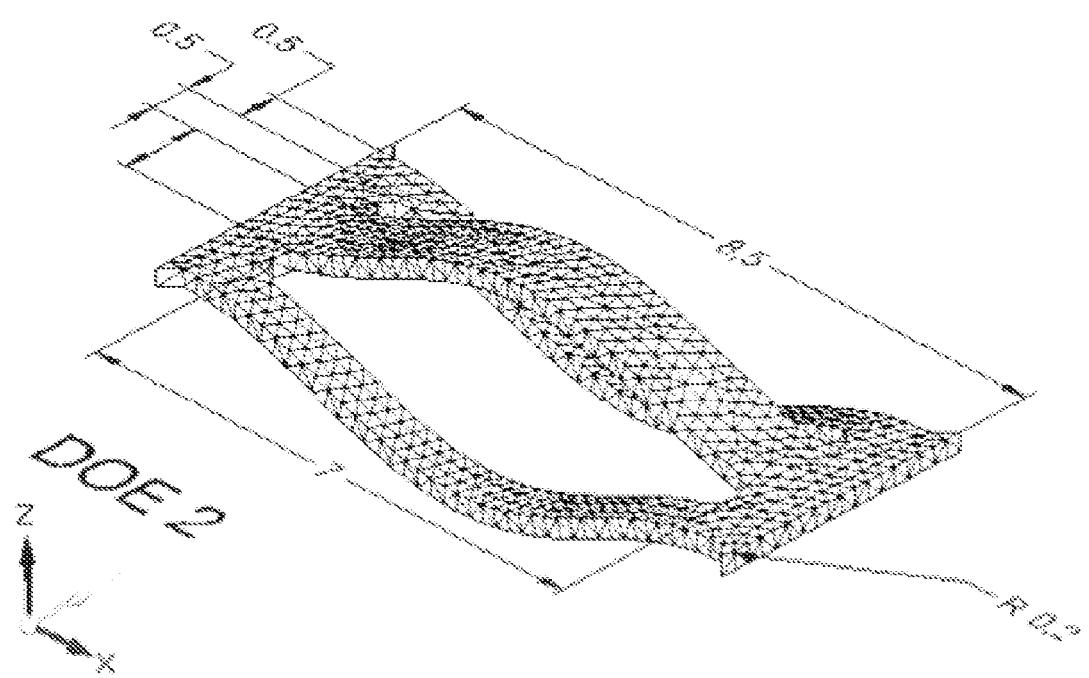

When selecting the dimension of the triple beam resonators used in this example, consideration was taken of the practical constraints of the experiments, such as process used and resulting reaction chamber volume. Reaction chamber volume was targeted as a maximum of 200 ul. As it was necessary to eliminate printing variability, only one set of PZT print artwork was used, this constraint therefore essentially fixing the size and gap between the 2 PZT pads. In turn, the beam length could not be any shorter than the gap between the PZT pads. Furthermore, the beam length could not be any longer than the overall distance, end to end, for the PZT pads. As such, some elements of the PZT pads reside on the resonant beam members. Groups of dimensions were investigated by FEA, selecting designs that had clear separation of peaks between mode 1 and 3. If they are too close together, immersion in liquid tends to make them merge into a single broad peak, making analysis difficult. An example of the FEA for triple beam resonator design 2 (cell 2 DPE) is shown in FIG. 8(a) and (b), wherein FIG. 8(a) shows Mode 1 at 16,436 Hz, while FIG. 8(b) shows Mode 3 at 18,347 Hz. It was noted that some of the elements in the beam mounting zone deflect upon modal analysis, indicating a dimension of 0 mm for parameter (d) (relating to the beam mounting zone) would not be feasible. This was confirmed experimentally, by comparing the response of a resonator (cell 39 DOE with beam length 8.5 mm) first with a 1.95 mm mounting zone, constructed by affixing a frame of 12.4 mm around the beams and then with a 0 mm mounting zone, by affixing a frame of 8.5 mm around the beams. The response with the 12.4 mm frame was found to have clear resonant peaks around 11 kHz and 26 kHz, while no resonant response was observed in the embodiment with the 8.5 mm frame.

(ii) Design Evaluation

Each sensor was fabricated and tested with a range of viscosity and density standards between 0.98-138 cP (centipoises) for viscosity and across a range of 1-1.4 for density.

Performance was measured using three methods (i) amplitude of measured peak above baseline (electrical earth), measured in decibels, (ii) frequency slope: the variation in frequency of response in liquid, and (iii) quality factor slope: the variation in quality factor of the response peak in liquid, measured at −3 dB below peak frequency.

The sensors were scanned from a low to a high frequency to identify resonant peaks and to determine the mode of frequency. The dominant mode was selected, and the sensor was challenged with a range of viscosity/density standard solutions.

(iii) Mode Analysis

Figure 9:
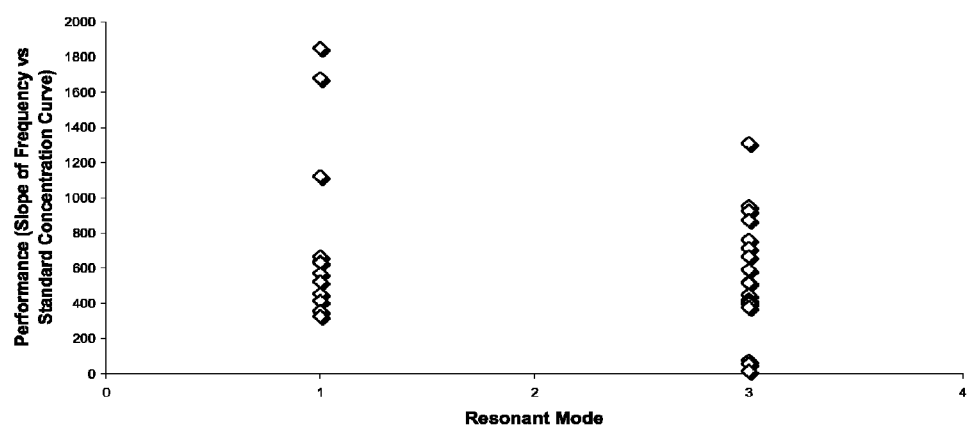
FIG. 9 shows a graph illustrating density/viscosity sensitivity of triple beam sensors comparing resonant modes against frequency response at resonant modes 1 and 3.

From the experimentation performed, identified clear differences in performance according to the dominant mode of the sensor. It is well know in the art that the density of liquid has a damping effect on resonating structures, reducing resonant frequency response. It is also well known in the art that viscosity can reduce the quality factor, by viscous coupling of the beams Comparing the frequency against the concentration response slope shows a clear difference in behaviour between mode 1 and mode 3. It can also be seen that overall, mode 1 offers the ability to have higher sensitivity to monitor changes in density than mode 3, although both modes can be used to gain a response. This is illustrated in FIG. 9 wherein the performance (in terms of the slope of frequency versus the standard concentration curve) is shown for resonant modes 1 and 3.

Mode 3 resonance is unique to a triple beam resonator, where the central beam is out of phase with the outer beams providing maximum probing of the sample.

Figure 10:
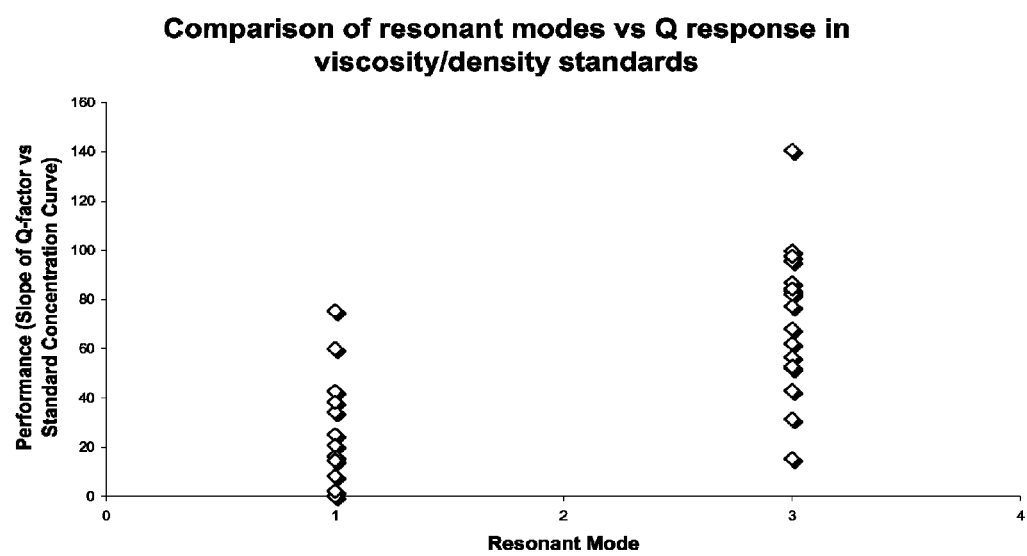
FIG. 10 shows a graph illustrating density/viscosity sensitivity of triple beam sensors comparing resonant modes against Q (quality factor) response at resonant modes 1 and 3.
Figure 11:
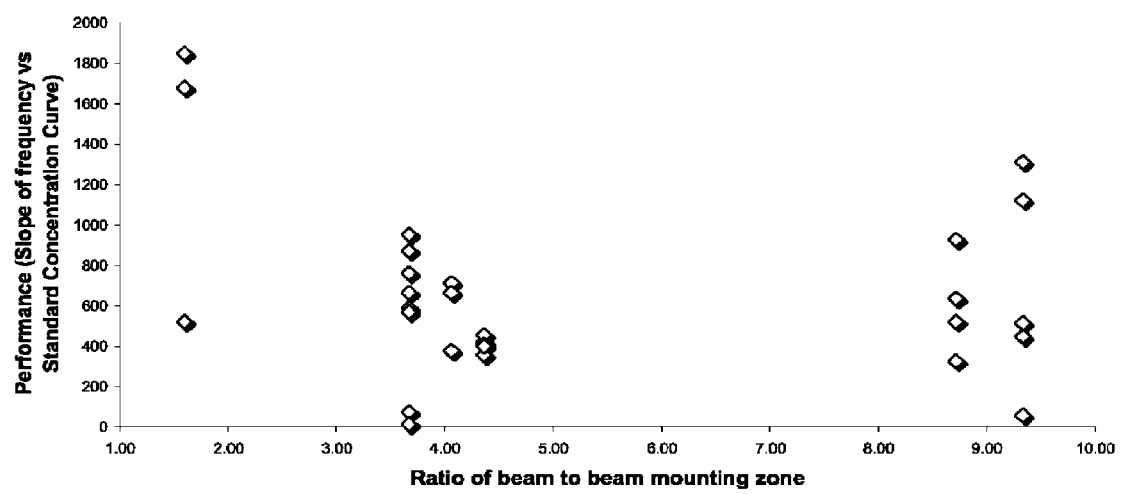
FIG. 11 shows a graph illustrating the relationship between the ratio of the beam length to beam mounting zones versus performance of triple beam sensors using frequency response slope with viscosity/density standard fluids.
Figure 12:
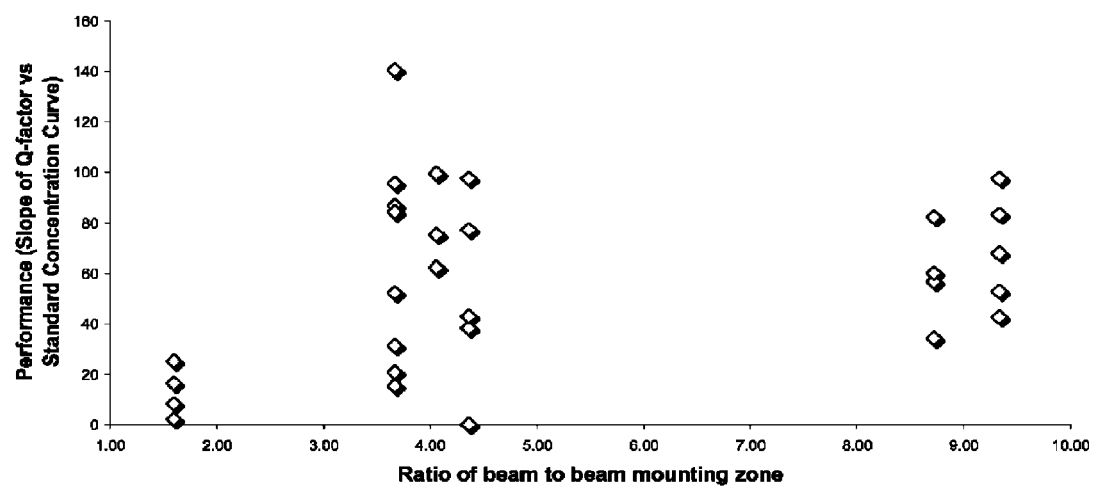
FIG. 12 shows a graph illustrating the relationship between the ratio of longitudinal beam length to the length of the beam mounting zone versus performance of triple beam sensors using quality factor response slope with viscosity/density standard fluids.
Figure 13:
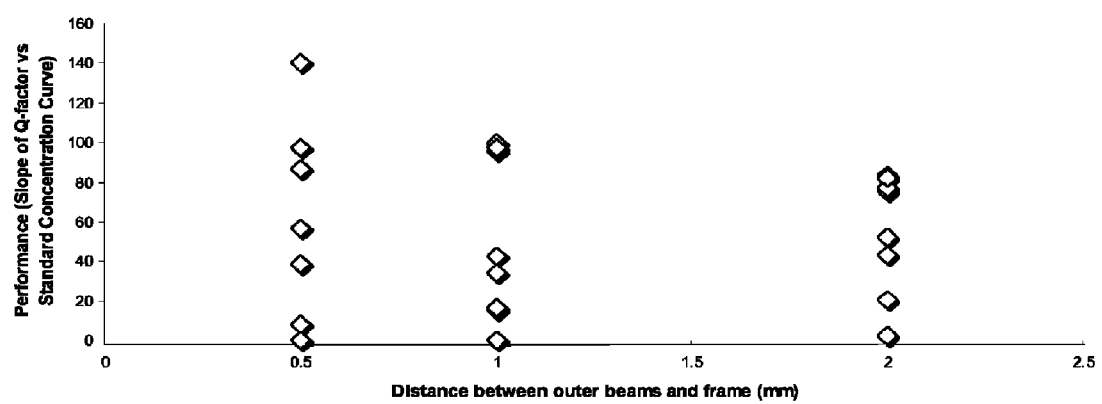
FIG. 13 shows a graph illustrating the relationship between the outer beam to frame distance versus performance of triple beam sensors using quality factor response slope with viscosity/density standard fluids.
Figure 14:
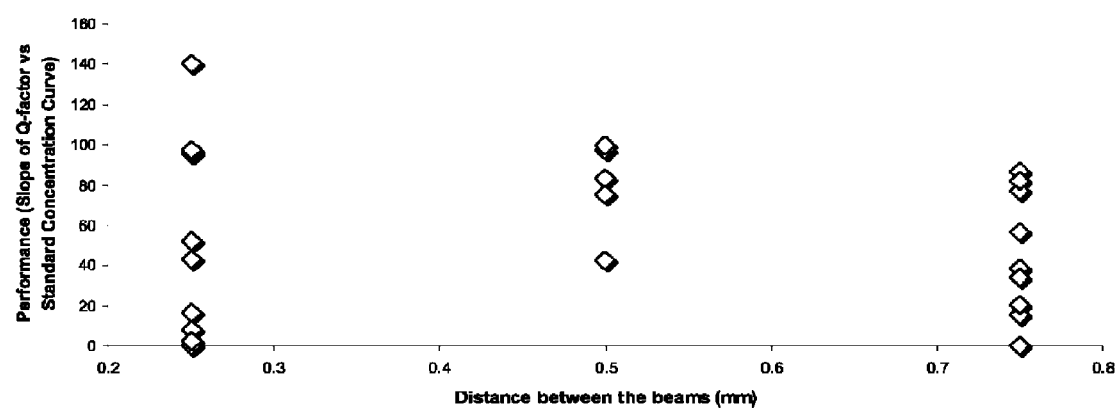
FIG. 14 shows a graph illustrating the relationship between sensitivity to viscosity standards against distance between the moving beams.

By comparing the quality factor against the concentration response, a clear differentiation can be observed between mode 1 and mode 3, this being shown in FIG. 10.

FIG. 10 shows that mode 3 offers the ability to have higher sensitivity to monitor changes in viscosity than mode 1. Double ended triple beam resonators offer the unique feature of a mode 3 resonance whereby the net forces at the ends of the beams cancel out, providing an improved sensor response as the out of phase transverse movement provide maximum shearing of the fluid sample surrounding the beam members.

By using an apparatus that measures the frequency and quality factor of a resonant peaks of a triple beam resonator, it was possible to obtain sensitive measurement of both density and viscosity of the fluid simultaneously.

(iv) Relationship of Beam Length to Beam Mounting Zone Length

As mentioned previously, the design of the triple beam resonators used in this example were limited by the requirement to keep to a single set of screen printed images in order minimise process impact on the results.

This resulted in the production of 6 families of resonators as previously described in FIGS. 7(a) to (f) and the table in FIG. 15. These families can be further summarized as per below.

Family 1: Beams having a ratio of beam length to beam mounting zone length of 1.59 (designs 4, 12, 20, 28, 36, 44). This family of beams showed an acceptable density sensitivity, with the frequency slopes varying between 500 to 1500 over the range. The viscosity sensitivity was however poor, with the quality factor slopes varying between 2 to 16 over the range. Mode 1 responses are the only measurable peaks. The gap to frame distance does not appear to affect the frequency response. The 1 mm width beams perform well, while the 2 mm width beams are completely dampened by the liquid sample.

Family 2: Beams having a ratio of beam length to beam mounting zone length of 3.67 (designs 1, 3, 9, 11, 17, 19, 25, 27, 33, 35, 41, 43). Designs 1 and 3 provide a high sensitivity to viscosity. 2 mm width beams are highly damped in liquid. 1 mm width beams give easy to measure peaks in water. Beams close to the outer frame give a higher sensitivity viscosity measurement. Devices with beams close together give high viscosity/density sensitivity. It is worth noting, that this group includes design 1 (cell 1 DOE), which was incorporated into a reaction chamber taking approximately 35 ul sample volume.

Family 3: Beams having a ratio of beam length to beam mounting zone length of 4.06 (designs 5, 13, 21, 29, 37, 45). Design 29 (2 mm central beam width design) has excellent sensitivity to density (frequency slope of 3104) and viscosity (quality factor slope of 264). However, on inspection of the raw data it was found that this was due to 2 peaks merging, meaning it would be difficult to develop an algorithm based on this performance at a later date. Design 5 (1 mm design), has similar performance. A 0.5 mm gap is present between the beams for both design 29 and 5. Both sets of results have been removed from the analysis graphs.

Family 4: Beams having a ratio of beam length to beam mounting zone length of 4.36 (designs 6, 7, 14, 15, 22, 23, 30, 31, 38, 39, 47). For each design the modes are close together and usually merge in liquid, distorting the measurement of quality factor. An example is device 15 (cell 15 DOE) where the two peaks merge at increasing concentrations and the quality factor is artificially lowered, increasing the slope of response.

Family 5: Beams having a ratio of beam length to beam mounting zone length of 8.72 (designs 8, 16, 24, 32, 40, 48). The viscosity performance is marginal: the maximum sensitivity is 82. Density performance is acceptable, producing a maximum frequency slope of 926 over the range. This geometry creates modes very close together and which are therefore hard to deconvolute without complex algorithms. An extra peak can be observed between the first and third mode which also makes measurement difficult.

Family 6: Beams having a ratio of beam length to beam mounting zone length of 9.33 (designs 2, 10, 18, 26, 34, 42). The viscosity performance less than 100. The density slope is 400 to 1300 over the range. The beams further from the frame appear to be better for the measurement of density. The beams closer to the frame produce a more sensitive response to viscosity. Very few devices in this group produce a useable response.

These results are summarized in FIGS. 11, 12, 13 and 14. A table setting out the dimensions of the triple beam resonators, as well as their viscosity and density value is shown in FIG. 15.

(v) Summary

Figure 16:
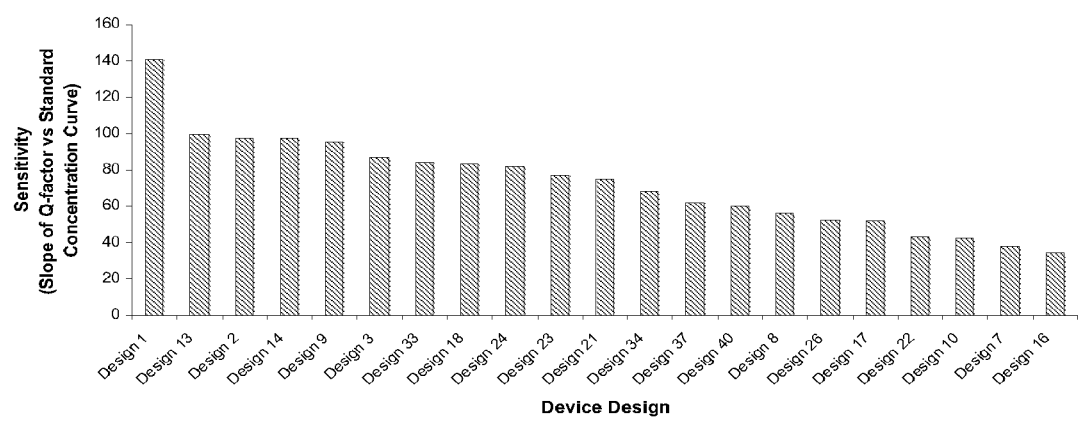
FIG. 16 shows a bar chart relating sensitivity to viscosity standards for high performing triple resonator designs as shown in FIG. 7 (for example Design 33 is equivalent to Cell 33 DOE of FIG. 7 and further to the designs listed in FIG. 15), where the devices are classified on the basis of the viscosity sensitivity based upon the slope of the Q-factor versus the standard concentration curve.
Figure 17:
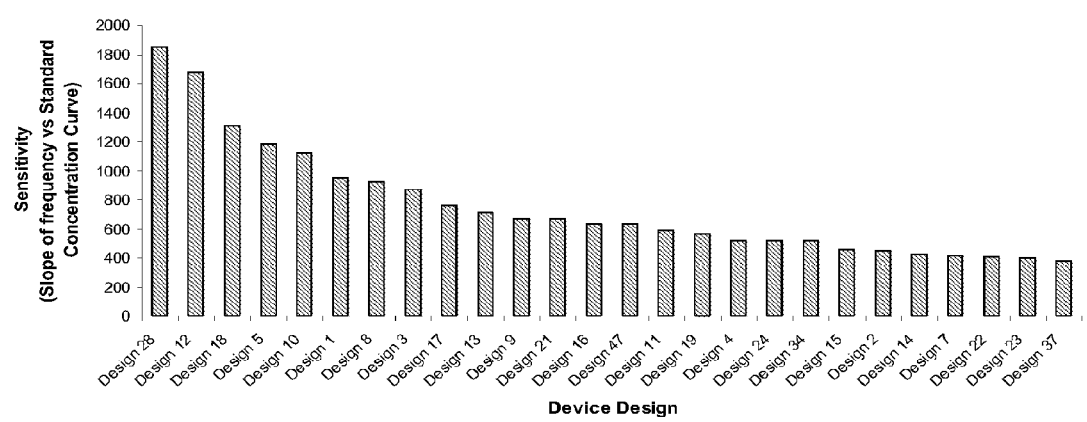
FIG. 17 shows a bar chart illustrating sensitivity to density standards for high performing triple resonator designs identified according to FIG. 7 (for example Design 21 is equivalent to Cell 21 DOE of FIG. 7) and further to the designs listed in FIG. 15, where the devices are classified on the basis of the sensitivity based upon the slope of the frequency versus the standard concentration curve.

In summary, a range of sensors were manufactured which were constructed according to example 1, but with the dimensions detailed hereinbefore. A number of high performing beam member designs were identified. These specific triple beam resonators are shown in FIG. 16 which shows a table of the best performing triple beam resonator devices when assessed with regard to density sensitivity, which is defined in relation to the slope of frequency standard concentration curve. FIG. 17 shows the best performing triple beam resonator devices when assessed with regard to sensitivity, which is defined in relation to the slope of frequency versus standard concentration curve.

From this analysis, a list of typical design features for a triple beam resonating structure for use in the present invention were identified for achieving enhanced measurement of density and viscosity: (i) Mode 3 is preferential for high sensitivity of measurement, (ii) Ratio of beam length to beam mounting zone length around 4 appears to be optimal, but a device with a ratio close to one up to a ratio close to 9 would still provide a measurement of some value, (iii) Both mode 1 and mode 3 used together can provide 2 sets of data from one response. A high performing resonating sensor can be made with a low sample volume—35 ul.

Example 3

Biosensor for Studying the Performance of Protein Removing Agents

The efficient removal of protein is an issue in many applications including medical devices and diagnostics, and selecting the optimal agent for removing protein can be difficult without a means of monitoring the progress of the removal. This is an example where the method of following a biochemical reaction using a triple beam resonator device according to the present invention can be of use.

A model protein (Limulus Amebocyte Lysate) or LAL was used in this example. A triple beam resonator was (design 9 (Cell 9 DOE) from FIG. 7 was selected, however other designs could have been selected) and fitted to a reaction chamber as described in Example 1. The response in air was measured, and several characteristics of the peak were measured as well as the frequency and the Q-factor.

The triple beam resonator was then incubated in a solution of protein LAL in the absence of endotoxin for two hours and allowed to dry in air. The response in air was measured, and several characteristics of the peak were measure to ascertain the amount of damping due to protein coating the beams: the frequency, Q-factor and phase angle.

A solution containing a commercially available protein removing agent used for cleaning soft contact lenses (2 mg of Trypsin, Lipase, Amylase in 2 ml of pyrogen free water) was added to the reaction chamber of the sensor. The reaction was run at 37° C. and the frequency response was measured for 12 minutes.

The sensor was rinsed to remove the cleaning solution and dried in air. The response in air was taken, and several characteristics of the peak were measured, the frequency, Q-factor (quality factor).

Results

The third order response of the resonator was used to assess loading of protein onto the beams. This mode causes the resonator beam members to move in a shearing, and as such material deposited between the beam members and on the surface of the beams will impede the motion of the beams.

Figure 18:
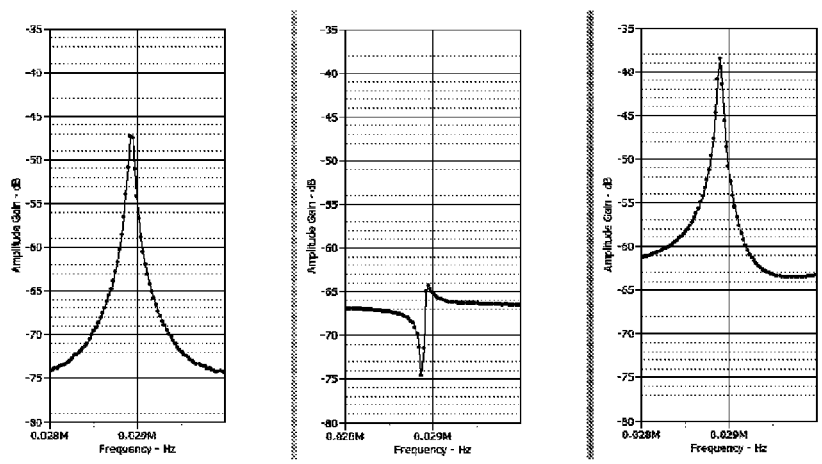
FIG. 18 shows 3 graphs illustrating the resonance spectra of a single triple beam resonator measured (left hand graph) before coating with protein, (middle graph) after coating in protein, (right hand graph) after treatment with a Trypsin, Lypase and Amylase solution.

FIG. 18 shows 3 graphs illustrating the resonance spectra of a single triple beam resonator measured (left hand graph) before coating with protein, (middle graph) after coating in protein, (right hand graph) after treatment with a Trypsin, Lipase and Amylase solution.

Initially prior to protein loading the resonating beam has a $3^{rd}$ order mode at 28.5 kHz with a quality factor of 904 and a 25 db gain. After incubation with protein for several hours the device was allowed to dry overnight. After this treatment the beams were heavily damped, and the resonant peak was reduce to a few decibels of gain, and was too low for the Q-factor to be calculated.

After treatment with a proprietary protein removing solution the peak frequency measured in air increased from a few db to over 20 db and the Q-factor was calculated to be 628.

Real Time Monitoring and Detection of a Enzymatic Reaction

It was possible to see the action of the enzymes breaking up the protein film that coat on the sensor in real time. The concentrated and viscous solution of enzyme preparation plus the protein film caused large viscous drag on the movement at the point of resonance, this created conditions for an "anti-phase" resonance measurement to become possible.

Figure 19:
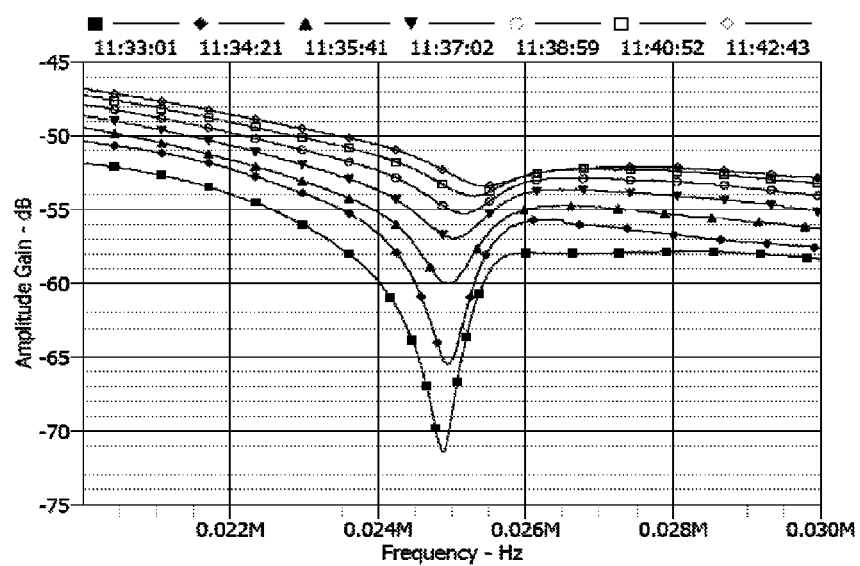
FIG. 19 shows a graph illustrating the real-time measurement of a protein film coating the resonator being removed using with a Trypsin, Lypase and Amylase solution.

FIG. 19 shows a graph illustrating the real-time measurement of a protein film coating the resonator being removed using with a Trypsin, Lypase and Amylase solution.

As shown in FIG. 19, the enzymes removed the protein from the surface, reducing the amount of protein coating the beams and enabling the beams to shear through the liquid with less resistance as time passed and the reaction occurred. It can be suggested that the amplitude of the anti-phase resonance is related to the amount of energy required by the device at its resonance.

Figure 20:
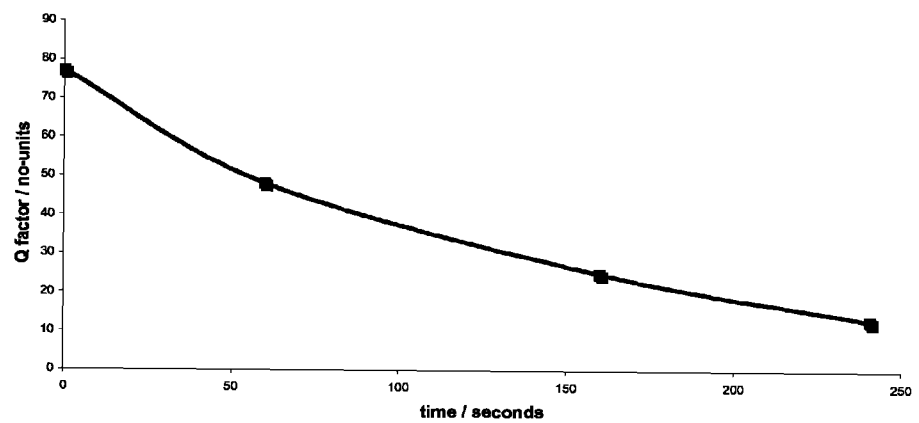
FIG. 20 shows a graph illustrating a change in Q factor of the anti-phase at 28.5 kHz against time, as the protein was removed from the triple-beam resonator by the action of a protein removal agent.

FIG. 20 shows a change in Q factor of the anti-phase at 28.5 kHz as the protein was removed from the triple-beam resonator by the action of the proprietary removal agent. It was therefore possible to calculate the Q factor of the device with respect to time (as shown in FIG. 20), which indicates the rate of reaction between the deposed protein and the enzymes.

The rate at which the Q factor, amplitude or phase angle or any combination of the three could be used to measure the rate of the reaction for a particular agent or reaction condition.

Example 4

Determination of Sugar Concentrations

The multi-beam resonating sensor, which in this embodiment comprises a triple beam sensor, was made according to the design described in Example 1

Preparation of Sugar Solutions

Materials used were household sugar (sucrose (Tate & Lyle)) and distilled water. The solutions were made by dissolving the required amount of sugar in distilled water with stirring to ensure all the crystals were dissolved.

Figure 21:
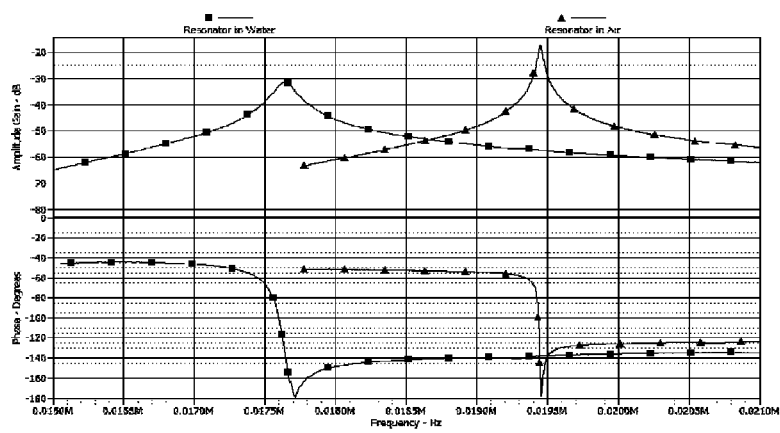
FIG. 21 shows the frequency response of the triple beam resonating sensor to water (FIG. 21(a)), and to air (FIG. 21(b))

The frequency response of the sensor was tested at 20° C. by measuring the frequency in air and water, as shown in FIG. 21(a) (air) and FIG. 21(b) (water).

As expected, the peak frequency drops from about 19,449 Hz to 17,638 Hz (a change of 1811 Hz), due to the increased damping on the triple beam afforded by the more dense water.

The Q factor also decreases from 720 to 137.8 with the change in viscosity and density between air and water 582.

Figure 22:
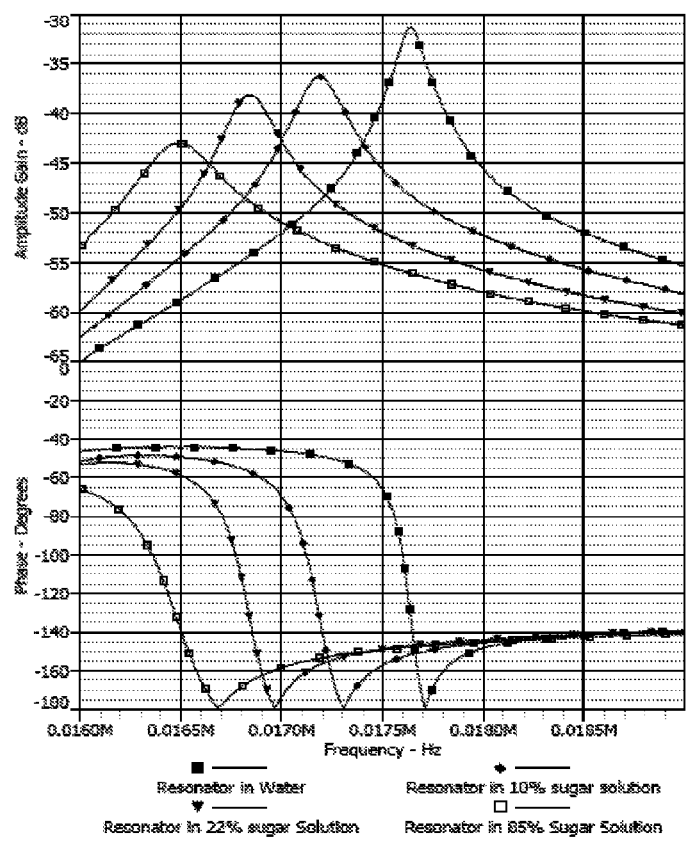
FIG. 22 shows the frequency response of the triple beam resonating sensor to sugar solutions of 0% and 85% w/v.

To enable sensor optimisation in future designs it is important that estimates of the viscosity changes are available. The viscosity-density product was calibrated using sugar solutions between 0 and 85% at 20° C., as shown in FIG. 22. The related sugar concentrations are shown below in Table 2.

TABLE 2

| Sugar concentrations | | | | |
|---|---|---|---|---|
| Sugar conc. % w/v | Density (l/kg) | Viscosity (mPa · S) | Frequency/ Hz | Q factor |
| 0 | 996.9 | 0.993 | 17,638 | 137.8 |
| 10.625 | 1032.3 | 1.33 | 17,188 | 74.73 |
| 42.5 | 1155.3 | 5.045 | 16,728 | 64.59 |
| 85 | 1420.882 | 138.41 | 16,489 | 45.05 |

Example 5

Detection of Endotoxin in a Test Sample

The experimentation in this example was performed in order to determine the effectiveness of the concept of detecting the reaction of *Limulus* amoebocyte lysate (LAL) with endotoxin within a liquid test sample, using a triple beam resonating microviscometer. In particular, the experimentation was used to determine that the sensor can distinguish between 2 different concentrations of endotoxin within a time period of 4 minutes.

(a) Materials and Methods:
Instrumentation
The following instrumentation was used:
Frequency Analyser and Amplifier (Cypher Instruments, London, UK)
Whirlimixer (Fisherbrand, UK)
QBD2 Heater (Grant, Shepreth, UK) and Thermal block (Almond Engineering, Livingston, UK)
Assay Reagents:
The following assay reagents were used: (i) Pyrogent™ *Limulus* amoebocyte lysate (LAL) reagent, (ii) Lonza, Walkersville, USA. Lot number #GL1176, (iii) Control Standard Endotoxin (CSE) raised in *E. Coli*. O55:B5, (iv) Lonza, Walkersville, USA. Lot number #'GL0983, (v) Lonza LAL Reagent Water (LRW). Lot number #01119129 Lonza, Walkersville, USA.

(b) Procedure for Gel Clot Testing
The sensors were depyrogenated using techniques well known to those skilled in the art. The CSE reagent was then reconstituted with LRW and diluted to working concentrations, as described by the manufacturer. A surfactant, Tween 20, was added at 0.05% as this was found to improve the stability of the endotoxin standards.

The sensor was "blocked" with LAL and LRW for 20 minutes before being rinsed and stored in the refrigerator prior to use.

The LAL lysate was reconstituted with LRW as per the manufacturers' specification. An aliquot of water containing CSE was mixed with LAL lysate at a ratio of 1:1, and then immediately dispensed into the sensor well. Immediately following the addition of the sample to the well, the analysis was performed.

The frequency analyser was configured to scan between 20 kHz and 30 kHz to obtain an initial air calibration reading. The output signal was attenuated by −7.5 db to remove any distortion. The test period was set to 23 ms per data point, the total run time was 12 minutes. This allows the capture of 1024 data points in 2 minutes. After each scan the analyser was set to immediately repeat the scan.

(c) Determination of Endotoxin
As shown in FIGS. 23(*a*) and 23(*b*), it is possible to observe the difference in the frequency response and phase curves for the 0.1 EU/ml and 0 EU/ml endotoxin reactions.

In FIG. 23(*a*) it can be seen that during the first four scans, the height and width of the response curve changes somewhat after each 80 second measurement: the peaks are becoming smaller and flatter. The peak frequency is decreasing slightly as the peaks are becoming flatter. Increasing amounts of energy are used to cause the structure to resonate. In FIG. 23(*b*) the height and width of the response curve change very slowly after each 80 second time point compared to 23(*a*). The change in the resonant peak size and shape with respect to time reflect the rate of reaction in the reaction chamber.

Figure 24:
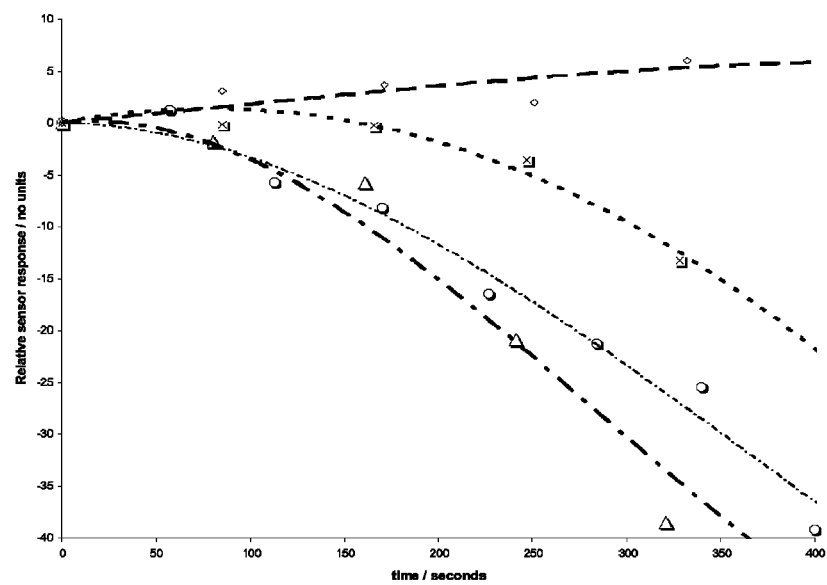
FIG. 24 shows that the sensor gives an output that corresponds to the concentration of endotoxin in the water sample. Q factor changes as the LAL reacts with the endotoxin. (Lines were labelled as follows: small diamonds, 0 EU/ml, boxes/crosses 0.1 EU/ML, spheres 1 EU/ml, and triangles 10 EU/ml)

FIG. 24 illustrates the relationship between relative Q factor measured over approximately 400 seconds, and the concentration of endotoxin in the sample. There is a clear definition between the four different endotoxin concentrations and Q factor response, with 0 EU/ml displaying an increase in relative Q factor due to evaporation and 10 EU/ml displaying a large decrease in Q factor in 80 seconds. At approximately 120 seconds the sensor response can distinguish between 0 EU/ml and 0.1 EU/ml.

Figure 25:
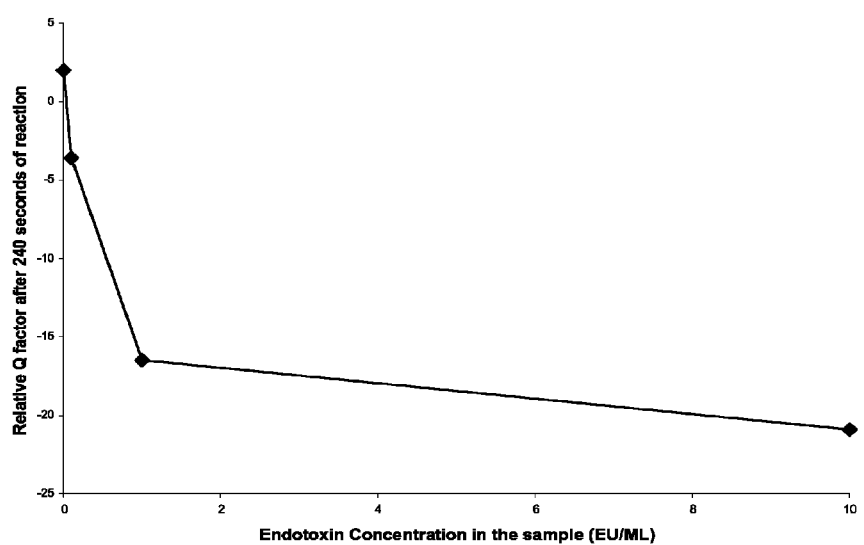
FIG. 25 shows that graph illustrating that a sensor gives an output that corresponds to the concentration of endotoxin in the water sample. Q factor changes as the LAL reacts with the endotoxin.

FIG. 25 illustrates the relationship between relative Q-factor measured at 240 seconds, and the concentration of endotoxin in the standard being analysed. It can be observed that biggest sensitivity to endotoxin is in the range of 0 EU/ml and 0.1 EU/ml.

Figure 26:
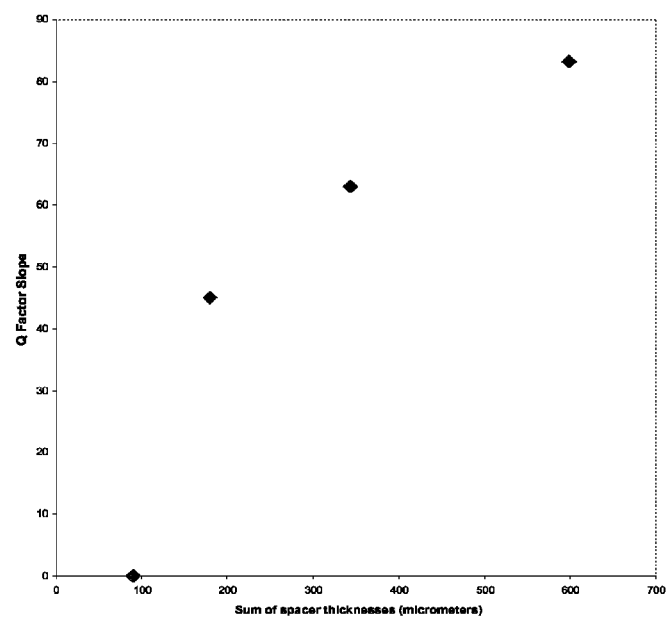
FIG. 26 illustrates the relationship between reaction chamber height and Q Factor response to viscosity/density standards.

FIG. 26 illustrates the relationship between reaction chamber height and Q factor response to viscosity/density standards in a sensor with 8.5 mm long beams. It can be observed that if a sensor is desired with improved sensitivity to viscosity or density, the most optimal response (greatest change) is with a reaction chamber height (with the resonator at the centre) for this particular design is at around 1 mm. However this device could use a reaction chamber height up to 1.4 mm successfully. Longer beam devices will require a substantially greater reaction chamber, potentially a reaction chamber of several millimeters to be optimally sensitive whilst a shorter beamed version would have an optimal response at a lower reaction chamber height.

All documents referred to in this specification are herein incorporated by reference. Various modifications and variations to the described embodiments of the inventions will be apparent to those skilled in the art without departing from the scope of the invention. Although the invention has been described in connection with specific embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. An apparatus for use in monitoring a change in a density and/or a viscosity of a test sample, comprising:
   a multi-beam resonator, the multi-beam resonator comprising:
      a base substrate comprising a mounting zone defined thereon having a defined longitudinal length;
      at least two resonant beam members, wherein each of the resonant beam members has a respective longitudinal length, wherein a ratio of the longitudinal length of each resonant beam member to the defined longitudinal length of the mounting zone of the base substrate is in a range of 1 to 9;
      at least one vibratory element positioned to cause a vibration of at least one of the resonant beam members;
      at least one sensor means for monitoring at least one parameter associated with the vibration of the resonant beam member; and
      a reaction chamber for receiving and retaining a test sample, the reaction chamber comprising at least one inlet port to allow an introduction of the test sample; and
   a reagent comprising amebocyte lysate or a synthetic analogue thereof for adding to the test sample to form a test sample mixture within the reaction chamber.

2. An apparatus as claimed in claim 1, wherein the resonant beam members are provided in a parallel arrangement and are fixed at each end of their respective longitudinal lengths to the base substrate.

3. An apparatus as claimed in claim 1, wherein the at least one inlet port allows the test sample to be introduced into the reaction chamber from a top of the reaction chamber.

4. An apparatus as claimed in claim 1, wherein at least one outlet port is provided in the reaction chamber, wherein the at least one outlet port is provided in an arrangement and of dimensions which are suitable to permit air to escape from the reaction chamber.

5. An apparatus as claimed in claim 1 wherein the ratio of the total longitudinal length of the resonant beam members to the length of the mounting zone of the multi-beam resonator which is defined on the base substrate is in the range of 1 to 9.

6. An apparatus as claimed in claim 1, wherein the ratio of the longitudinal length of each of the resonant beam members to the defined longitudinal length of the mounting zone of the multi-beam resonator is about 4.

7. An apparatus as claimed in claim 1, wherein a distance of a spacing between an outer lateral side of an outermost resonant beam member and an innermost wall of a surrounding housing is 5 mm or less.

8. An apparatus as claimed in claim 1, wherein a distance of a spacing between an outer lateral side of an outermost resonant beam member and an innermost wall of a surrounding housing is 0.5 mm or less.

9. An apparatus as claimed in claim 1, wherein a distance of a spacing between an outer lateral side of an outermost resonant beam member and an innermost wall of a surrounding housing is greater than 25 μm.

10. An apparatus as claimed in claim 1, wherein an internal height of the reaction chamber is greater than 1 mm.

11. An apparatus as claimed in claim 1, wherein the multi-beam resonator comprises three resonant beam members, wherein one of the three resonant beam members is a central resonant beam member located between the other two resonant beam members, wherein a width of the central resonant beam member in a lateral direction is about 2 mm or less.

12. An apparatus as claimed in claim 1, wherein the multi-beam resonator comprises three resonant beam members, wherein one of the three resonant beam members is a central resonant beam member located between the other two resonant beam members, wherein a width of the central resonant beam member in a lateral direction is 1 mm.

13. An apparatus as claimed in claim 1, wherein the multi-beam resonator comprises three resonant beam members, wherein one of the three resonant beam members is a central resonant beam member located between the other two resonant beam members, wherein two of the three resonant beam members are outer resonant beam members located on an outside of the central resonant beam member, wherein each resonant beam member has a lateral width, and wherein the lateral width of the central resonant beam member is a sum of the lateral widths of the outer resonant beam members.

14. An apparatus as claimed in claim 1, wherein the longitudinal length of at least one of the resonant beam members is 18 mm or less.

15. An apparatus as claimed in claim 1, wherein the longitudinal length of at least one of the resonant beam members is about 5.5 mm or less.

16. An apparatus as claimed in claim 1, wherein the resonant beam members are provided in a parallel arrangement, and wherein a distance of a spacing between resonant beam members is 2 mm or less.

17. An apparatus as claimed in claim 1, wherein a total longitudinal length of the multi-beam resonator is 20 mm or less.

18. An apparatus as claimed in claim 1, wherein a surface of at least part of the reaction chamber is provided with a coating selected from the group of: a hydrophobic coating and a hydrophilic coating.

19. A test strip comprising:
a multi-beam resonator, the multi-beam resonator comprising:
a base substrate comprising a mounting zone defined thereon having a defined longitudinal length;
at least two resonant beam members, wherein each of the resonant beam members has a respective longitudinal length, wherein a ratio of the respective longitudinal length of each resonant beam member to the defined longitudinal length of the mounting zone of the base substrate is in a range of 1 to 9;
at least one vibratory element positioned to cause a vibration of at least one of the beam members;
at least one sensor means for monitoring at least one parameter associated with the vibration of the resonant beam member; and
a reaction chamber for receiving and retaining a test sample, the reaction chamber comprising at least one inlet port to allow an introduction of the test sample; and
a reagent comprising amebocyte lysate or a synthetic analogue thereof for adding to the test sample to form a test sample mixture within the reaction chamber.

20. An apparatus as claimed in claim 1, wherein the amebocyte lysate or the synthetic analogue thereof comprises *Limulus* amebocyte lysate (LAL) or a synthetic analogue thereof or *Tachypleus* amebocyte lysate (TAL) or a synthetic analogue thereof.

21. An apparatus as claimed in claim 1, wherein the reagent is provided in a dried form.

22. An apparatus as claimed in claim 1, wherein at least one surface of the reaction chamber is at least partially coated with the reagent.

23. An apparatus as claimed in claim 1, wherein the reagent is a dried amebocyte lysate or synthetic analogue thereof which is provided within the reaction chamber and is reconstituted following addition of a liquid test sample.

24. An apparatus as claimed in claim 1, wherein the amebocyte lysate or synthetic analogue thereof is provided in a liquid solution.

25. An apparatus as claimed in claim 1, wherein the amebocyte lysate or synthetic analogue thereof is added to the reaction chamber prior to, simultaneously, or following loading of the reaction chamber with test sample.

26. An apparatus as claimed in claim 1, comprising the test sample mixture, the test sample mixture being formed by mixing the test sample with the amebocyte lysate or the synthetic analogue thereof prior to loading the test sample mixture into the reaction chamber.

27. An apparatus as claimed in claim 1, wherein the multi-beam resonator comprises at least three resonant beam members.

28. An apparatus as claimed in claim 1, wherein the reaction chamber defines a static volume and allows a defined amount of test sample to be retained within the reaction chamber.

29. An apparatus as claimed in claim 28, wherein an internal volume of the reaction chamber is less than 1000 μl.

30. An apparatus as claimed in claim 1, wherein the at least one sensor means is configured to monitor the at least one parameter within a time period of 60 seconds or less.

31. An apparatus as claimed in claim 2, wherein the resonant beam members are an integral part of the base substrate.

32. An apparatus as claimed in claim 1, wherein the sensor means comprises a sensor means for monitoring at least one parameter selected from the group of resonant frequency, quality factor, resonant phase angle, change in resonant frequency, change in quality factor, change in resonant phase angle, rate of change of resonant frequency, rate of change of quality factor, and rate of change in resonant phase angle.

33. An apparatus as claimed in claim 1, wherein the at least one parameter is used to generate a signal to indicate a presence or an absence of bacterial endotoxin in the test sample.

34. An apparatus as claimed in claim 1, wherein the resonant beam members are substantially composed of inert material.

35. An apparatus as claimed in claim 34, wherein the inert material is selected from the group of silicon, copper, palladium, platinum, steel, and stainless steel.

36. An apparatus as claimed in claim 1, wherein the at least one vibratory element is a piezoelectric element.

37. An apparatus as claimed in claim 36, wherein the piezoelectric element comprises piezoelectric material selected from the group of a polymer, PVDF, a crystal, a ceramic, PZT, and a screen printed PZT.

38. An apparatus for monitoring a change in a density and/or a viscosity of a test sample comprising a multi-beam resonator,
the multi-beam resonator comprising:
a base substrate comprising a mounting zone defined thereon having a defined longitudinal length;
at least two resonant beam members, wherein each of the resonant beam members has a respective longitudinal length, wherein a ratio of the longitudinal length of each resonant beam member to the defined longitudinal length of the mounting zone of the base substrate is in a range of 1 to 9;
at least one vibratory element positioned to cause a vibration of at least one of the resonant beam members,
at least one sensor means for monitoring at least one parameter associated with the vibration of the resonant beam member,
a reaction chamber for receiving and retaining a test sample, the reaction chamber comprising at least one inlet port to allow an introduction of the test sample.

39. An apparatus as claimed in claim 38, wherein a ratio of the longitudinal length of each of the resonant beam members to the defined longitudinal length of the mounting zone of the multi-beam resonator is about 4.

40. An apparatus as claimed in claim 38 wherein a distance of a spacing between an outer lateral side of an outermost resonant beam member and an innermost wall of a surrounding housing is 5 mm or less.

41. An apparatus as claimed in claim 38 wherein an internal height of the reaction chamber is greater than 1 mm.

42. An apparatus as claimed in claim 38 wherein the multi-beam resonator comprises three resonant beam members, wherein one of the three resonant beam members is a central resonant beam member located between the other two resonant beam members, wherein a width of the central resonant beam member in the lateral direction is about 2 mm or less.

43. An apparatus as claimed in claim 38 wherein the multi-beam resonator comprises three resonant beam members, wherein one of the three resonant beam members is a central resonant beam member located between the other two resonant beam members, wherein two of the three resonant beam members are outer resonant beam members located on an outside of the central resonant beam member, wherein each resonant beam member has a lateral width, and wherein the lateral width of the central beam member is a sum of the lateral widths of the outer beam members.

44. An apparatus as claimed in claim 38 wherein the longitudinal length of at least one of the resonant beam members is 18 mm or less.

45. An apparatus as claimed in claim 38 wherein the resonant beam members are provided in a parallel arrangement, and wherein a distance of a spacing between resonant beam members is 2 mm or less.

46. An apparatus as claimed in claim 38 wherein a total longitudinal length of the multi-beam resonator is 20 mm or less.

* * * * *